United States Patent
Josien et al.

(10) Patent No.: US 9,278,965 B2
(45) Date of Patent: Mar. 8, 2016

(54) BRIDGED AND FUSED ANTIDIABETIC COMPOUNDS

(71) Applicant: Merck Sharp & Dohme Corp., Rahway, NJ (US)

(72) Inventors: Hubert B. Josien, Jersey City, NJ (US); John W. Clader, Milton, VT (US); William J. Greenlee, Teaneck, NJ (US); Michael J. Mayer, Glen Burnie, MD (US); Jason L. Davis, Albany, NY (US); Shuangyi Wan, Pittsburgh, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/044,316

(22) Filed: Oct. 2, 2013

(65) Prior Publication Data

US 2014/0038970 A1 Feb. 6, 2014

Related U.S. Application Data

(63) Continuation of application No. 13/145,152, filed as application No. PCT/US2010/021586 on Jan. 21, 2010, now abandoned.

(60) Provisional application No. 61/146,868, filed on Jan. 23, 2009.

(51) Int. Cl.

| C07D 417/14 | (2006.01) |
|---|---|
| C07D 263/44 | (2006.01) |
| C07D 277/34 | (2006.01) |
| C07D 417/04 | (2006.01) |
| C07D 417/12 | (2006.01) |

(52) U.S. Cl.
CPC ............ *C07D 417/14* (2013.01); *C07D 263/44* (2013.01); *C07D 277/34* (2013.01); *C07D 417/04* (2013.01); *C07D 417/12* (2013.01)

(58) Field of Classification Search
CPC ... C07D 417/14; C07D 277/34; C07D 263/44
USPC ......................................................... 514/248
See application file for complete search history.

(56) References Cited

U.S. PATENT DOCUMENTS

| 2005/0245529 A1 | 11/2005 | Stemkamp et al. |
| 2006/0258728 A1 | 11/2006 | Tani et al. |
| 2007/0265332 A1 | 11/2007 | Ge et al. |
| 2011/0312995 A1 | 12/2011 | Josien et al. |

FOREIGN PATENT DOCUMENTS

| WO | 2004/058174 A1 | 7/2004 |
| WO | 2006/083612 A1 | 8/2006 |
| WO | 2006/083781 A1 | 8/2006 |
| WO | 2008/054674 A1 | 5/2008 |
| WO | 2010/085522 A1 | 7/2010 |
| WO | 2010/085525 A1 | 7/2010 |
| WO | 2010/091176 A1 | 8/2010 |

OTHER PUBLICATIONS

Garrido, D. M., et al., "Synthesis and activity of small molecule GPR40 agonists", Bioorganic & Medicnial Chemistry Letters, vol. 16, (2006), pp. 1840-1845.
International Search Report for PCT/US2010/021586, dated May 18, 2010.
International Preliminary Report on Patentability for PCT/US2010/021586, dated Jul. 26, 2011.

*Primary Examiner* — Paul V Ward
(74) *Attorney, Agent, or Firm* — Anna L. Cocuzzo; Catherine D. Fitch

(57) ABSTRACT

This invention provides for certain bridged and fused compounds of the formula

G-L-A    I or a pharmaceutically acceptable salt, ester of solvate thereof wherein:

A is

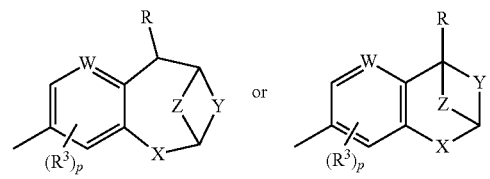

and the other variables are defined herein; the inventive compounds are agonists of the G-protein coupled receptor 40 (GPR40, also known as free fatty acid receptor FFAR). This invention further relates to pharmaceutical compositions containing these compounds, and the use of these compounds to regulate insulin levels in a mammal. The compounds may be used, for example in the prevention and treatment of Type 2 diabetes mellitus and in the prevention and treatment of conditions related to Type 2 diabetes mellitus, such as insulin resistance, obesity and lipid disorders.

10 Claims, No Drawings

BRIDGED AND FUSED ANTIDIABETIC COMPOUNDS

CROSS-REFERENCE TO RELATED APPLICATIONS

This application is a continuation application of U.S. application Ser. No. 13/145,152, which is a U.S. National Phase application under 35 U.S.C. §371 of PCT/US2010/021586, filed Jan. 21, 2010, and claims priority from U.S. provisional application 61/146,868, filed Jan. 23, 2009.

FIELD OF THE INVENTION

The present invention relates to certain bridged and fused compounds that are agonists of the G-protein coupled receptor 40 (GPR40, also known as free fatty acid receptor FFAR), pharmaceutical compositions containing the compounds, and the use of these compounds to regulate insulin levels in a mammal. The compounds may be used, for example in the prevention and treatment of Type 2 diabetes mellitus and in the prevention and treatment of conditions related to Type 2 diabetes mellitus, such as insulin resistance, obesity and lipid disorders.

BACKGROUND OF THE INVENTION

Diabetes refers to a disease state or process derived from multiple causative factors and is characterized by elevated levels of plasma glucose (hyperglycemia) in the fasting state or after administration of glucose during a glucose tolerance test. Persistent or uncontrolled hyperglycemia is associated with a wide range of pathologies. Diabetes mellitus, is associated with elevated fasting blood glucose levels and increased and premature cardiovascular disease and premature mortality. It is also related directly and indirectly to various metabolic conditions, including alterations of lipid, lipoprotein, apolipoprotein metabolism and other metabolic and hemodynamic diseases. As such, the diabetic patient is at increased risk of macrovascular and microvascular complications. Such complications can lead to diseases and conditions such as coronary heart disease, stroke, peripheral vascular disease, hypertension, nephropathy, neuropathy, and retinopathy. Accordingly, therapeutic control and correction of glucose homeostasis is regarded as important in the clinical management and treatment of diabetes mellitus.

There are two generally recognized forms of diabetes. In Type 1 diabetes, or insulin-dependent diabetes mellitus (IDDM), the diabetic patient's pancreas is incapable of producing adequate amounts of insulin, the hormone which regulates glucose uptake and utilization by cells. In Type 2 diabetes, or noninsulin dependent diabetes mellitus (NIDDM), patients often produce plasma insulin levels comparable to those of nondiabetic subjects; however, the cells of patients suffering from type 2 diabetes develop a resistance to the effect of insulin, even in normal or elevated plasma levels, on glucose and lipid metabolism, especially in the main insulin-sensitive tissues (muscle, liver and adipose tissue).

Insulin resistance is not associated with a diminished number of cellular insulin receptors but rather with a post-insulin receptor binding defect that is not well understood. This cellular resistance to insulin results in insufficient insulin activation of cellular glucose uptake, oxidation, and storage in muscle, and inadequate insulin repression of lipolysis in adipose tissue, and of glucose production and secretion in the liver. A net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Patients who have insulin resistance often have several symptoms that together are referred to as Syndrome X, or the metabolic syndrome. According to one widely used definition, a patient having metabolic syndrome is characterized as having three or more symptoms selected from the group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III or ATP III), National Institutes of Heath, 2001, NIH Publication No. 01-3670. Patients with metabolic syndrome, whether or not they have increase risk of developing the macrovascular and microvascular complications that occur with Type 2 diabetes, such as atherosclerosis and coronary heart disease.

The available treatments for Type 2 diabetes, some of which have not changed substantially in many years, are used alone and in combination. Many of these treatments have recognized limitations, however. For example, while physical exercise and reductions in dietary intake of fat, high glycemic carbohydrates, and calories can dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic beta-cells to secrete more insulin, and/or by injection of insulin when sulfonylureas or meglitinide become ineffective, can result in insulin concentrations high enough to stimulate insulin-resistance in tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a separate class of agents that can increase insulin sensitivity and bring about some degree of correction of hyperglycemia. These agents, however, can induce lactic acidosis, nausea and diarrhea.

The glitazones (i.e. 5-benzylthiazolidine-2,4-diones) are another class of compounds that have proven useful for the treatment of Type 2 diabetes. These agents increase insulin sensitivity in muscle, liver and adipose tissue in several animal models of type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-γ subtype. PPAR-γ agonism is generally believed to be responsible for the improved insulin sensititization that is observed with the glitazones. Newer PPAR agonists that are being tested for treatment of Type 2 diabetes are agonists of the alpha, gamma or delta subtype, or a combination thereof, and in many cases are chemically different from the glitazones (i.e., they are not thiazolidinediones). Serious side effects (e.g. liver toxicity) have been noted in some patients treated with glitazone drugs, such as troglitazone.

Compounds that are inhibitors of the dipeptidyl peptidase-IV (DPP-IV) enzyme are also under investigation as drugs that may be useful in the treatment of diabetes, and particularly Type 2 diabetes.

Additional methods of treating hyperglycemia and diabetes are currently under investigation. New biochemical approaches include treatment with alpha-glucosidase inhibitors (e.g. acarbose), protein tyrosine phosphatase-1B (PTP-1B) inhibitors, and glucagon receptor antagonists.

The free fatty acid receptor GPR40 (FFAR or FFAR1) is part of a family of recently deorphanized GPCR's that bind fatty acids of varying chain lengths. GPR40 binds long-chain FFA, particularly oleate, as well as the PPAR-gamma agonist rosiglitazone. GPR40 is highly expressed in the pancreas, where it functions to produce insulin release upon agonist stimulation through activation of the PKC pathway resulting in Ca++ efflux. The receptor is also expressed in throughout the brain in monkeys and humans, but not in rodents.

Initial studies in GPR40 KO mice reported that they were resistant to high-fat diet-induced insulin resistance, suggesting an antagonist mechanism would be appropriate for this target. However, given the localization and function of the receptor, as well as the fact that most groups have not replicated this initial finding, the use of an agonist appears to be the appropriate answer for increasing insulin release for the treatment of diabetes. In facts, it has been demonstrated that agonists of GPR40 stimulate glucose-dependent insulin secretion in vitro and lower an elevated blood glucose level in vivo. See for example, Diabetes 2008, 57, 2211; J. Med. Chem. 2007, 50, 2807.

Compounds that act as GPR40 receptor agonists are known in the art. WO2008/054674 (assigned to Merck) discloses bicyclic derivatives of the formula

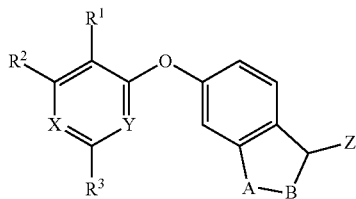

These derivatives are said to be useful in treating Type 2 diabetes mellitus and conditions associated with the disease, including insulin resistance, obesity and lipid disorders. WO2006/083781, WO2006/083612, US 2007/0265332 and WO2008/054674 (all assigned to Merck) disclose bicyclic derivatives that modulate the GPR40 receptor and are said to treat Type-2 diabetes.

Other bicyclic derivatives are known in the art to be useful in treating disease states such as diabetes, obesity and metabolic disorder. WO 2004/058174 (assigned to Bayer) discloses indane acetic acid derivatives of the formula

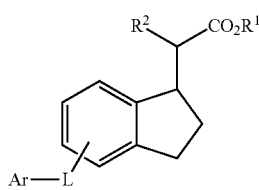

and states that these derivatives are useful in treating Type-2 diabetes, obesity and atherosclerotic diseases.

US 2005/0245529 (Boehringer Ingelheim) discloses alkyne derivatives that are said to be useful in treating metabolic disorders and diabetes by antagonizing the MCH-receptor.

There is a need for new compounds, formulations, treatments and therapies to treat diseases and disorders associated with the GPR40 receptor that exhibit good safety profiles and efficacy by controlling insulin levels in a mammal. It is, therefore, an object of this invention to provide compounds that are useful in the treatment or prevention or amelioration of diseases and disorders associated with the GPR40 receptor, such as hyperglycemia, diabetes, and related metabolic diseases and indications.

SUMMARY OF THE INVENTION

In its many embodiments, the present invention provides for a novel class of bridged and fused heterocyclic compounds that are agonists of the GPR40 receptor, or metabolites, stereoisomer, salts, solvates or polymorphs thereof, methods of preparing such compounds, pharmaceutical compositions comprising one or more of such compounds, methods of preparing pharmaceutical formulations compromising one or more such compounds, and methods of treatment, prevention, inhibition or amelioration of one or more conditions associated with compounds that act as agonists of the GRP40 receptor.

In one aspect, the present application discloses a compound, or pharmaceutically acceptable salts, esters, metabolites, solvates, prodrugs or polymorphs of said compound, said compound having the general structure shown in the Formula:

$$G-L-A \qquad\qquad I$$

or a pharmaceutically acceptable salt, ester of solvate thereof wherein

G is aryl, arylalkyl, heteroaryl, or heteroarylalkyl, which are optionally substituted by at least one (for example 1 to 5 or 1 to 3) $R^2$;

L is —O—, —C(O)—, —S(O)$_q$—, or —N($R^3$)—;

A is

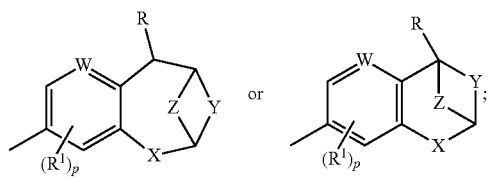

W is —C— or —N—;

X is a bond, —O—, —C(O)—, —S(O)$_q$, —C($R^a$)($R^b$)— or —N($R^8$)—;

Y is a bond, —[C($R^a$)($R^b$)]$_n$—O—[C($R^a$)($R^b$)]$_n$, —[C($R^a$)($R^b$)]$_n$—C(O)—[C($R^a$)($R^b$)]$_n$, —[C($R^a$)($R^b$)]$_n$—S(O)$_q$—[C($R^a$)($R^b$)]$_n$, —[C($R^a$)($R^b$)]$_m$— or —N($R^8$)—;

Z is a bond, —[C($R^a$)($R^b$)]$_n$—O—[C($R^a$)($R^b$)]$_n$, —[C($R^a$)($R^b$)]$_n$—C(O)—[C($R^a$)($R^b$)]$_n$, —[C($R^a$)($R^b$)]$_n$—S(O)$_q$—[C($R^a$)($R^b$)]$_n$, —[C($R^a$)($R^b$)]$_m$— or —N($R^8$)—;

R is a group selected from the group consisting of (i)
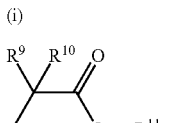

(ii)
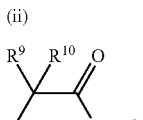

(iii)
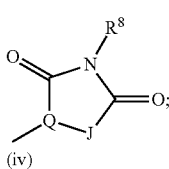

(iv)
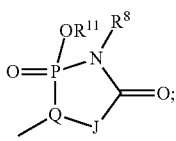

and
(v) tetrazolyl,
wherein
Q is —CH— or —N—, and
J is —S—, —CH$_2$—, —O— or —N(R$^8$)—;

R$^a$ is independently selected from the group consisting of H, —OH, halo, alkoxy, alkyl, cycloalkyl, and cycloalkylalkyl;

R$^b$ is independently selected from the group consisting of H, —OH, halo, alkoxy, alkyl, cycloalkyl, and cycloalkylalkyl;

R$^1$ is independently selected from the group consisting of H, halogen, —SF$_5$, —CN, —NO$_2$, —N(R$^6$)(R$^7$), —OH, alkyl, alkoxy, cycloalkyl, cycloalkyloxy, cycloalkylalkyl, cycloalkylalkoxy, and —S(O)$_q$-alkyl, wherein said alkyl, alkoxy, cycloalkyl, cycloalkyloxy, cycloalkylalkyl, and cycloalkylalkoxy are optionally substituted with one or more (for example 1 to 5 or 1 to 3) groups selected from the group consisting of —OH, halo, alkyl, —S(O)$_q$-alkyl, haloalkyl, alkoxy, haloalkoxy, and cycloalkyl;

R$^2$ is independently selected from the group consisting of halogen, —SF$_5$, —CN, —NO$_2$, —N(R$^6$)(R$^7$), —OH, alkyl, alkoxy, cycloalkyl, cycloalkyloxy, cycloalkylalkyl, cycloalkylalkoxy, aryl, arylalkyl, heteroaryl, heteroarylalkyl and —S(O)$_q$-alkyl, wherein said alkyl, alkoxy, cycloalkyl, cycloalkyloxy, cycloalkylalkyl, cycloalkylalkoxy, aryl, arylalkyl, heteroaryl, and heteroarylalkyl are optionally substituted with one or more (for example 1 to 5 or 1 to 3) groups selected from the group consisting of —OH, halo, alkyl, —S(O)$_q$-alkyl, haloalkyl, alkoxy, haloalkoxy, and cycloalkyl;

R$^3$ is independently selected from the group consisting of H, alkyl and haloalkyl;

R$^4$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

R$^5$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

R$^6$ is independently selected from the group consisting of H, alkyl, cycloalkyl, cycloalkylalkyl, aryl, arylalkyl, heterocycloalkyl, heterocycloalkylalkyl, heteroaryl and heteroarylalkyl;

R$^7$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

or R$^6$ and R$^7$ together form a 4- to 7-membered heterocycloalkyl or a 5- or 5-membered heteroaryl ring optionally having, in addition to the N atom, 1 or 2 heteroatoms selected from the group consisting of O, N(R$^8$), N or S, wherein said rings are optionally substituted by one or more (for example 1 to 5 or 1 to 3) R$^{12}$ moieties;

R$^8$ is independently selected from the group consisting of H, alkyl, cycloalkyl, cycloalkylalkyl, aryl, arylalkyl, heterocycloalkyl, heterocycloalkylalkyl, heteroaryl, heteroarylalkyl, —C(O)—R$^5$, —C(O)O—R$^5$, —C(O)N(R$^6$)(R$^7$), —C(O)-alkylene-OR$^4$, —C(O)-alkylene-N(R$^6$)(R$^7$), —C(O)-alkylene-S(O)$_q$—R$^5$, —S(O)$_q$—R$^5$, —S(O)$_q$-alkylene-OR$^4$, —S(O)$_q$-alkylene-N(R$^6$)(R$^7$), -alkylene-OR$^4$, -alkylene-S(O)$_q$—R$^5$, -alkylene-N(R$^6$)(R$^7$), and —S(O)$_2$N(R$^6$)(R$^7$) wherein said alkyl, cycloalkyl, cycloalkylalkyl, aryl, arylalkyl, heterocycloalkyl, heterocycloalkylalkyl, heteroaryl, heteroarylalkyl and alkylene are optionally substituted with one or more (for example 1 to 5 or 1 to 3) groups selected from the group consisting of —OH, halo, alkyl, haloalkyl, alkoxy, haloalkoxy and cycloalkyl;

R$^9$ is independently selected from the group consisting of H, alkyl, haloalkyl;

R$^{10}$ is independently selected from the group consisting of H, —OH, alkyl, alkyl, cycloalkyl or alkoxy wherein said alkyl, alkyl, cycloalkyl or alkoxy groups are optionally substituted with at least one (for example 1 to 5 or 1 to 3) substituents selected from the group consisting of halo and —OR$^5$;

R$^{11}$ is independently selected from the group consisting of H, alkyl, and haloalkyl;

wherein each of the alkyl, cycloalkyl, cycloalkylalkyl, aryl, arylalkyl, heterocycloalkyl, heterocycloalkylalkyl, heteroaryl, and heteroarylalkyl groups in R$^4$, R$^5$, R$^6$ and R$^7$ are independently unsubstituted or substituted by one or more (for example 1 to 5 or 1 to 3) R$^{12}$ groups, where R$^{12}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —N(R$^5$)(R$^6$), —C(O)N(R$^6$)(R$^7$), and —S(O)$_2$N(R$^6$)(R$^7$), —NO$_2$, —SF$_5$, —CN, and halo and wherein each alkyl, cycloalkyl, cycloalkylalkyl, aryl, arylalkyl, heterocycloalkyl, heterocycloalkylalkyl, heteroaryl, and heteroarylalkyl group in R$^{12}$ is independently unsubstituted or substituted by one or more (for example 1 to 5 or 1 to 3) R$^{13}$ groups where R$^{13}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —C(O)N(R$^6$)(R$^7$), and —S(O)$_2$N(R$^6$)(R$^7$), —NO$_2$, —SF$_5$, —CN, and halo;

m is independently 1, 2, or 3;
n is independently 0, 1 or 2;
q is independently 0, 1, or 2; and
p is 0, 1, 2, or 3,
provided that Y and Z cannot be a bond at the same time.

In another aspect, the present application provides for a pharmaceutical composition comprising a pharmaceutically effective amount of compound of Formula I or a pharmaceutically acceptable salt, ester, solvate or prodrug thereof and a pharmaceutically acceptable carrier.

In yet another aspect, the present application provides for a method for controlling insulin levels in a mammal (e.g., human) in need thereof which comprises administering an effective amount of a compound of Formula I or a pharmaceutically acceptable salt, ester, solvate, or prodrug thereof to said mammal (e.g., human).

Another aspect of the present invention is to provide for a method for the prevention or treatment of Type-2 diabetis mellitus in a mammal (e.g., human) in need thereof which comprises administering an effective amount of a compound of Formula I or a pharmaceutically acceptable salt, ester, solvate, or prodrug thereof to said mammal (e.g., human).

Another aspect of the present invention is to provide for a method for the prevention or treatment of conditions related to Type-2 diabetis mellitus (e.g., insulin resistance, obesity and lipid disorders) in a mammal (e.g., human) in need there of which which comprises administering an effective amount of a compound of Formula I or a pharmaceutically acceptable salt, ester, solvate, or prodrug thereof to said mammal (e.g., human).

Another aspect of the present invention is to provide for a method for the prevention or treatment of Syndrome X in a mammal (e.g., human) in need thereof which comprises administering an effective amount of a compound of Formula I or a pharmaceutically acceptable salt, ester, solvate, or prodrug thereof to said mammal (e.g., human).

DETAILED DISCUSSION

In an embodiment, the present invention discloses certain bridged and fused heterocyclic compounds that are represented by structural Formula I, or a pharmaceutical acceptable salt, ester, solvate or prodrug thereof, wherein the various moieties are described above.

In one embodiment, the present invention discloses compounds of Formula Ia, which are represented by the structural formula

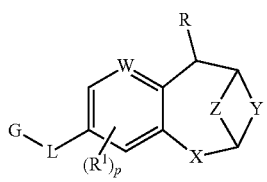

Ia or a pharmaceutically acceptable salt, ester, solvate or prodrug thereof,
G is aryl, arylalkyl, heteroaryl, or heteroarylalkyl, which is optionally substituted by at least one $R^2$;
L is —O—, —C(O)—, —S(O)$_q$—, or —N($R^3$)—;
W is —C— or —N—;
X is a bond, —O—, —C(O)—, —S(O)$_q$, —C($R^a$)($R^b$)— or —N($R^8$)—;

Y is a bond, —[C($R^a$)($R^b$)]$_n$—O—[C($R^a$)($R^b$)]$_n$, —[C($R^a$)($R^b$)]$_n$—C(O)—[C($R^a$)($R^b$)]$_n$, —[C($R^a$)($R^b$)]$_n$—S(O)$_q$—[C($R^a$)($R^b$)]$_n$, —[C($R^a$)($R^b$)]$_m$— or —N($R^8$)—;
Z is a bond, —[C($R^a$)($R^b$)]$_n$—O—[C($R^a$)($R^b$)]$_n$, —[C($R^a$)($R^b$)]$_n$—C(O)—[C($R^a$)($R^b$)]$_n$, —[C($R^a$)($R^b$)]$_n$—S(O)$_q$—[C($R^a$)($R^b$)]$_n$, —[C($R^a$)($R^b$)]$_m$— or —N($R^8$)—;
R is a group selected from the group consisting of (i)

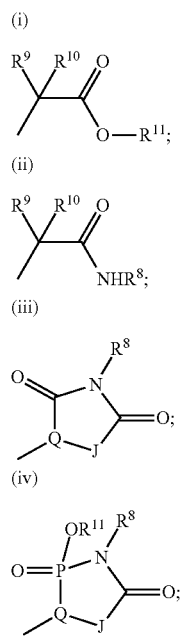

(ii)

(iii)

(iv)

and
(v) tetrazolyl,
wherein
Q is —CH— or —N—, and
J is —S—, —CH$_2$—, —O— or —N($R^8$)—;
$R^a$ is independently selected from the group consisting of H, —OH, halo, alkoxy, alkyl, cycloalkyl, and cycloalkylalkyl;
$R^b$ is independently selected from the group consisting of H, —OH, halo, alkoxy, alkyl, cycloalkyl, and cycloalkylalkyl;
$R^1$ is independently selected from the group consisting of H, halogen, —SF$_5$, —CN, —NO$_2$, —N($R^6$)($R^7$), —OH, alkyl, alkoxy, cycloalkyl, cycloalkyloxy, cycloalkylalkyl, cycloalkylalkoxy, and —S(O)$_q$-alkyl, wherein said alkyl, alkoxy, cycloalkyl, cycloalkyloxy, cycloalkylalkyl, and cycloalkylalkoxy are optionally substituted with one or more groups selected from the group consisting of —OH, halo, alkyl, —S(O)$_q$-alkyl, haloalkyl, alkoxy, haloalkoxy, and cycloalkyl;
$R^2$ is independently selected from the group consisting of halogen, —SF$_5$, —CN, —NO$_2$, —N($R^6$)($R^7$), —OH, alkyl, alkoxy, cycloalkyl, cycloalkyloxy, cycloalkylalkyl, cycloalkylalkoxy, aryl, arylalkyl, heteroaryl, heteroarylalkyl and —S(O)$_q$-alkyl, wherein said alkyl, alkoxy, cycloalkyl, cycloalkyloxy, cycloalkylalkyl, cycloalkylalkoxy, aryl, arylalkyl, heteroaryl, and heteroarylalkyl are optionally substituted with one or more groups selected from the group consisting of —OH, halo, alkyl, —S(O)$_q$-alkyl, haloalkyl, alkoxy, haloalkoxy, and cycloalkyl;

$R^3$ is independently selected from the group consisting of H, alkyl and haloalkyl;

$R^4$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

$R^5$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

$R^6$ is independently selected from the group consisting of H, alkyl, cycloalkyl, cycloalkylalkyl, aryl, arylalkyl, heterocycloalkyl, heterocycloalkylalkyl, heteroaryl and heteroarylalkyl;

$R^7$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

or $R^6$ and $R^7$ together form a 4- to 7-membered heterocycloalkyl or a 5- or 5-membered heteroaryl ring optionally having, in addition to the N atom, 1 or 2 heteroatoms selected from the group consisting of O, $N(R^8)$, N or S, wherein said rings are optionally substituted by one or more $R^{12}$ moieties;

$R^8$ is independently selected from the group consisting of H, alkyl, cycloalkyl, cycloalkylalkyl, aryl, arylalkyl, heterocycloalkyl, heterocycloalkylalkyl, heteroaryl, heteroarylalkyl, —C(O)—$R^5$, —C(O)O—$R^5$, —C(O)N($R^6$)($R^7$), —C(O)-alkylene-O$R^4$, —C(O)-alkylene-N($R^6$)($R^7$), —C(O)-alkylene-S(O)$_q$—$R^5$, —S(O)$_q$—$R^5$, —S(O)$_q$-alkylene-O$R^4$, —S(O)$_q$-alkylene-N($R^6$)($R^7$), -alkylene-O$R^4$, -alkylene-S(O)$_q$—$R^5$, -alkylene-N($R^6$)($R^7$), and —S(O)$_2$N($R^6$)($R^7$) wherein said alkyl, cycloalkyl, cycloalkylalkyl, aryl, arylalkyl, heterocycloalkyl, heterocycloalkylalkyl, heteroaryl, heteroarylalkyl and alkylene are optionally substituted with one or more groups selected from the group consisting of —OH, halo, alkyl, haloalkyl, alkoxy, haloalkoxy and cycloalkyl;

$R^9$ is independently selected from the group consisting of H, alkyl, haloalkyl;

$R^{10}$ is independently selected from the group consisting of H, —OH, alkyl, alkyl, cycloalkyl or alkoxy wherein said alkyl, alkyl, cycloalkyl or alkoxy groups are optionally substituted with at least one substituent selected from the group consisting of halo and —O$R^5$;

$R^{11}$ is independently selected from the group consisting of H, alkyl, and haloalkyl;

wherein each of the alkyl, cycloalkyl, cycloalkylalkyl, aryl, arylalkyl, heterocycloalkyl, heterocycloalkylalkyl, heteroaryl, and heteroarylalkyl groups in $R^4$, $R^5$, $R^6$ and $R^7$ are independently unsubstituted or substituted by one or more $R^{12}$ groups, where $R^{12}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —O$R^4$, —C(O)—$R^5$, —C(O)O—$R^5$, —S(O)$_q$—$R^5$, —N($R^5$)($R^6$), —C(O)N($R^6$)($R^7$), and —S(O)$_2$N($R^6$)($R^7$), —NO$_2$, —SF$_5$, —CN, and halo and wherein each alkyl, cycloalkyl, cycloalkylalkyl, aryl, arylalkyl, heterocycloalkyl, heterocycloalkylalkyl, heteroaryl, and heteroarylalkyl group in $R^{12}$ is independently unsubstituted or substituted by one or more $R^{13}$ groups where $R^{13}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —O$R^4$, —C(O)—$R^5$, —C(O)O—$R^5$, —S(O)$_q$—$R^5$, —C(O)N($R^6$)($R^7$), and —S(O)$_2$N($R^6$)($R^7$), —NO$_2$, —SF$_5$, —CN, and halo;

m is independently 1, 2, or 3;
n is independently 0, 1 or 2;
q is independently 0, 1, or 2; and
p is 0, 1, 2, or 3, provided that Y and Z cannot both be a bond at the same time.

In another embodiment, the present invention discloses compounds of Formula I, which are represented by the structural Formula

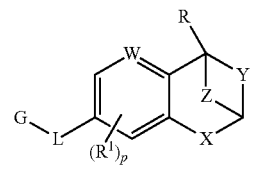

Ib or a pharmaceutically acceptable salt, ester, solvate or prodrug thereof,

G is aryl, arylalkyl, heteroaryl, or heteroarylalkyl, which is optionally substituted by at least one $R^2$;

L is —O—, —C(O)—, —S(O)$_q$—, or —N($R^3$)—;

W is —C— or —N—;

X is a bond, —O—, —C(O)—, —S(O)$_q$, —C($R^a$)($R^b$)— or —N($R^8$)—;

Y is a bond, —[C($R^a$)($R^b$)]$_n$—O—[C($R^a$)($R^b$)]$_n$, —[C($R^a$)($R^b$)]$_n$—C(O)—[C($R^a$)($R^b$)]$_n$, —[C($R^a$)($R^b$)]$_n$—S(O)$_q$—[C($R^a$)($R^b$)]$_n$, —[C($R^a$)($R^b$)]$_m$— or —N($R^8$)—;

Z is a bond, —[C($R^a$)($R^b$)]$_n$—O—[C($R^a$)($R^b$)]$_n$, —[C($R^a$)($R^b$)]$_n$—C(O)—[C($R^a$)($R^b$)]$_n$, —[C($R^a$)($R^b$)]$_n$—S(O)$_q$—[C($R^a$)($R^b$)]$_n$, —[C($R^a$)($R^b$)]$_m$— or —N($R^8$)—;

R is a group selected from the group consisting of (i)

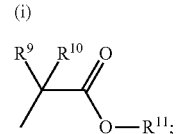

(ii)

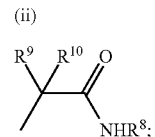

(iii)

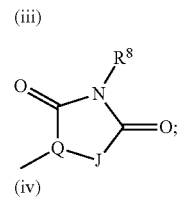

(iv)

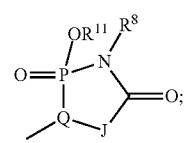

and (v) tetrazolyl wherein

Q is —CH— or —N—, and

J is —S—, —CH$_2$—, —O— or —N(R$^8$)—;

R$^a$ is independently selected from the group consisting of H, —OH, halo, alkoxy, alkyl, cycloalkyl, and cycloalkylalkyl;

R$^b$ is independently selected from the group consisting of H, —OH, halo, alkoxy, alkyl, cycloalkyl, and cycloalkylalkyl;

R$^1$ is independently selected from the group consisting of H, halogen, —SF$_5$, —CN, —NO$_2$, —N(R$^6$)(R$^7$), —OH, alkyl, alkoxy, cycloalkyl, cycloalkyloxy, cycloalkylalkyl, cycloalkylalkoxy, and —S(O)$_q$-alkyl, wherein said alkyl, alkoxy, cycloalkyl, cycloalkyloxy, cycloalkylalkyl, and cycloalkylalkoxy are optionally substituted with one or more groups selected from the group consisting of —OH, halo, alkyl, —S(O)$_q$-alkyl, haloalkyl, alkoxy, haloalkoxy, and cycloalkyl;

R$^2$ is independently selected from the group consisting of halogen, —SF$_5$, —CN, —NO$_2$, —N(R$^6$)(R$^7$), —OH, alkyl, alkoxy, cycloalkyl, cycloalkyloxy, cycloalkylalkyl, cycloalkylalkoxy, aryl, arylalkyl, heteroaryl, heteroarylalkyl and —S(O)$_q$-alkyl, wherein said alkyl, alkoxy, cycloalkyl, cycloalkyloxy, cycloalkylalkyl, cycloalkylalkoxy, aryl, arylalkyl, heteroaryl, and heteroarylalkyl are optionally substituted with one or more groups selected from the group consisting of —OH, halo, alkyl, —S(O)$_q$-alkyl, haloalkyl, alkoxy, haloalkoxy, and cycloalkyl;

R$^3$ is independently selected from the group consisting of H, alkyl and haloalkyl;

R$^4$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

R$^5$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

R$^6$ is independently selected from the group consisting of H, alkyl, cycloalkyl, cycloalkylalkyl, aryl, arylalkyl, heterocycloalkyl, heterocycloalkylalkyl, heteroaryl and heteroarylalkyl;

R$^7$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

or R$^6$ and R$^7$ together form a 4- to 7-membered heterocycloalkyl or a 5- or 5-membered heteroaryl ring optionally having, in addition to the N atom, 1 or 2 heteroatoms selected from the group consisting of O, N(R$^8$), N or S, wherein said rings are optionally substituted by one or more R$^{12}$ moieties;

R$^8$ is independently selected from the group consisting of H, alkyl, cycloalkyl, cycloalkylalkyl, aryl, arylalkyl, heterocycloalkyl, heterocycloalkylalkyl, heteroaryl, heteroarylalkyl, —C(O)—R$^5$, —C(O)O—R$^5$, —C(O)N(R$^6$)(R$^7$), —C(O)-alkylene-OR$^4$, —C(O)-alkylene-N(R$^6$)(R$^7$), —C(O)-alkylene-S(O)$_q$—R$^5$, —S(O)$_q$—R$^5$, —S(O)$_q$-alkylene-OR$^4$, —S(O)$_q$-alkylene-N(R$^6$)(R$^7$), -alkylene-OR$^4$, -alkylene-S(O)$_q$—R$^5$, -alkylene-N(R$^6$)(R$^7$), and —S(O)$_2$N(R$^6$)(R$^7$) wherein said alkyl, cycloalkyl, cycloalkylalkyl, aryl, arylalkyl, heterocycloalkyl, heterocycloalkylalkyl, heteroaryl, heteroarylalkyl and alkylene are optionally substituted with one or more groups selected from the group consisting of —OH, halo, alkyl, haloalkyl, alkoxy, haloalkoxy and cycloalkyl;

R$^9$ is independently selected from the group consisting of H, alkyl, haloalkyl;

R$^{10}$ is independently selected from the group consisting of H, —OH, alkyl, alkyl, cycloalkyl or alkoxy wherein said alkyl, alkyl, cycloalkyl or alkoxy groups are optionally substituted with at least one substituent selected from the group consisting of halo and —OR$^5$;

R$^{11}$ is independently selected from the group consisting of H, alkyl, and haloalkyl;

wherein each of the alkyl, cycloalkyl, cycloalkylalkyl, aryl, arylalkyl, heterocycloalkyl, heterocycloalkylalkyl, heteroaryl, and heteroarylalkyl groups in R$^4$, R$^5$, R$^6$ and R$^7$ are independently unsubstituted or substituted by one or more R$^{12}$ groups, where R$^{12}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —N(R$^5$)(R$^6$), —C(O)N(R$^6$)(R$^7$), and —S(O)$_2$N(R$^6$)(R$^7$), —NO$_2$, —SF$_5$, —CN, and halo and wherein each alkyl, cycloalkyl, cycloalkylalkyl, aryl, arylalkyl, heterocycloalkyl, heterocycloalkylalkyl, heteroaryl, and heteroarylalkyl group in R$^{12}$ is independently unsubstituted or substituted by one or more R$^{13}$ groups where R$^{13}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —C(O)N(R$^6$)(R$^7$), and —S(O)$_2$N(R$^6$)(R$^7$), —NO$_2$, —SF$_5$, —CN, and halo;

m is independently 1, 2, or 3;

n is independently 0, 1 or 2;

q is independently 0, 1, or 2; and p is 0, 1, 2, or 3, provided that Y and Z cannot both be a bond at the same time.

An embodiment of the present invention is a compound of Formula Ia where W is —CH—.

Another embodiment of the present invention is a compound of Formula Ia where X is a bond.

Another embodiment of the present invention is a compound of Formula Ia where X is a —CH$_2$—.

Another embodiment of the present invention is a compound of Formula Ia where X is a —O—.

Another embodiment is a compound of Formula Ia where Y is bond.

Another embodiment is a compound of Formula Ia where Y is —CH$_2$—.

Another embodiment is a compound of Formula Ia where Y is —CH$_2$—CH$_2$—.

Another embodiment is a compound of Formula Ia where Z is a bond.

Another embodiment is a compound of Formula Ia where Z is —CH$_2$—.

Another embodiment is a compound of Formula Ia where Z is —CH$_2$—CH$_2$—.

Another embodiment is a compound of Formula Ia where W is —CH— and R$^1$ is halogen, cyano or —SF$_5$ and p is 1.

Another embodiment is a compound of Formula Ia where G is aryl; for example, phenyl or naphthyl.

Another embodiment is where G is heteroaryl; for example, pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, benzofurazanyl, indolyl, azaindolyl, benzimidazolyl, benzothienyl, quinolinyl, imidazolyl, thienopyridyl, quinazolinyl, thienopyrimidyl, isoquinolinyl, benzoazaindolyl, 1,2,4-triazinyl, benzothiazolyl.

Another embodiment is a compound of Formula Ia where G is phenyl or naphthyl and $R^2$ is absent.

Another embodiment is a compound of Formula Ia where G is phenyl or naphthyl that is substituted by one or two $R^2$ groups, which independently are haloalkyl (e.g., trifluorormethyl), —$SF_5$, cyano or halo (e.g., fluoro or chloro).

Another embodiment is a compound of Formula Ia where G is pyrimidinyl, pyridyl, or thiazolyl and $R^2$ is absent.

Another embodiment is a compound of Formula Ia where G is pyrimidinyl, pyridyl, or thiazolyl that is substituted by one or two $R^2$ groups, which independently are haloalkyl (e.g., trifluorormethyl), —$SF_5$, cyano or halo (e.g., fluoro or chloro).

Another embodiment is a compound of Formula Ia where R is —$CH_2$—C(O)—OH.

Another embodiment is a compound of Formula Ia where R is —$CH_2$—C(O)—O($C_1$-$C_4$)alkyl.

Another embodiment is a compound of Formula Ia where R is —$CH_2$—C(O)—$NH_2$.

Another embodiment is a compound of Formula Ia where R is

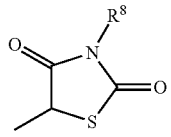

and $R^8$ is H or —($C_1$-$C_4$)alkyl.

Another embodiment is a compound of Formula Ia where R is

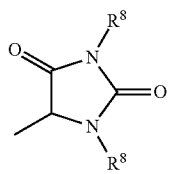

and $R^8$ is independently H or —($C_1$-$C_4$)alkyl.

Another embodiment is a compound of Formula Ia where R is

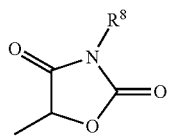

and $R^8$ is H or —($C_1$-$C_4$)alkyl.

Another embodiment is a compound of Formula Ia where R is

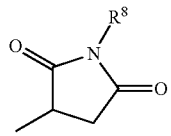

and $R^8$ is H or —($C_1$-$C_4$)alkyl.

Another embodiment is a compound of Formula Ia where R is

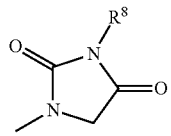

and $R^8$ is H or —($C_1$-$C_4$)alkyl.

Another embodiment is a compound of Formula Ia where R is

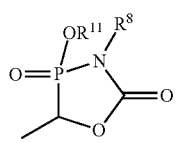

$R^8$ is H or —($C_1$-$C_4$)alkyl and $R^{11}$ is $R^8$ is H or —($C_1$-$C_4$)alkyl.

Another embodiment is a compound of Formula Ia where R is

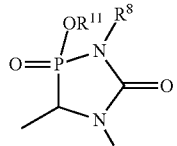

$R^8$ is independently H or —($C_1$-$C_4$)alkyl and $R^{11}$ is $R^8$ is H or —($C_1$-$C_4$)alkyl.

Another embodiment is a compound of Formula Ia where R is

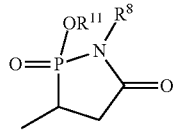

$R^8$ is H or —($C_1$-$C_4$)alkyl and $R^{11}$ is $R^8$ is H or —($C_1$-$C_4$)alkyl.

Another embodiment is a compound of Formula Ia where R is

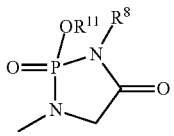

R[8] is H or —(C$_1$-C$_4$)alkyl and R[11] is R[8] is H or —(C$_1$-C$_4$)alkyl.

Another embodiment is a compound of Formula Ia where R is tetrazolyl.

Another embodiment is a compound of Formula Ia where L is —O—.

Another embodiment is a compound of Formula Ia where L is —N(R[3])— and R[3] is H or (C$_1$-C$_4$)alkyl or halo-(C$_1$-C$_4$)-alkyl.

Another embodiment is a compound of Formula Ia where R[2] absent or R[2] is H, haloalkyl (e.g., trifluoromethyl) or halo.

An embodiment of the present invention is a compound of Formula Ib where W is —CH—.

Another embodiment of the present invention is a compound of Formula Ib where X is a bond.

Another embodiment is a compound of Formula Ib where Y is —O—.

Another embodiment is a compound of Formula Ib where Y is —CH$_2$—.

Another embodiment is a compound of Formula Ib where Z is a bond.

Another embodiment is a compound of Formula Ib where Z is —O—.

Another embodiment is a compound of Formula Ib where Z is —CH$_2$—.

Another embodiment is a compound of Formula Ib where Y is a bond.

Another embodiment is a compound of Formula Ib where Y is —O—.

Another embodiment is a compound of Formula Ib where Y is —CH$_2$—.

Another embodiment is a compound of Formula Ib where W is —CH— and R[1] is halogen, cyano or —SF$_5$ and p is 1.

Another embodiment is a compound of Formula Ib where G is aryl; for example, phenyl or naphthyl.

Another embodiment is a compound of Formula Ib where G is heteroaryl; for example, pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, benzofurazanyl, indolyl, azaindolyl, benzimidazolyl, benzothienyl, quinolinyl, imidazolyl, thienopyridyl, quinazolinyl, thienopyrimidyl, isoquinolinyl, benzoazaindolyl, 1,2,4-triazinyl, benzothiazolyl.

Another embodiment is a compound of Formula Ib where G is phenyl or naphthyl and R[2] is absent.

Another embodiment is a compound of Formula Ib where G is phenyl or naphthyl that is substituted by one or two R[2] groups, which independently are haloalkyl (e.g., trifluorormethyl), —SF$_5$, cyano or halo (e.g., fluoro or chloro).

Another embodiment is a compound of Formula Ib where G is pyrimidinyl, pyridyl, or thiazolyl and R[2] is absent.

Another embodiment is a compound of Formula Ib where G is pyrimidinyl, pyridyl, or thiazolyl that is substituted by one or two R[2] groups, which independently are haloalkyl (e.g., trifluorormethyl), —SF$_5$, cyano or halo (e.g., fluoro or chloro).

Another embodiment is a compound of Formula Ib where R is —CH$_2$—C(O)—OH.

Another embodiment is a compound of Formula Ib where R is —CH$_2$—C(O)—O(C$_1$-C$_4$)alkyl.

Another embodiment is a compound of Formula Ib where R is —CH$_2$—C(O)—NH$_2$.

Another embodiment is a compound of Formula Ib where R is

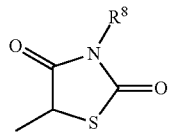

and R[8] is H or —(C$_1$-C$_4$)alkyl.

Another embodiment is a compound of Formula Ib where R is

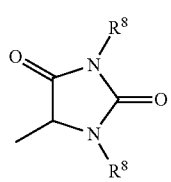

and R[8] is independently H or —(C$_1$-C$_4$)alkyl.

Another embodiment is a compound of Formula Ib where R is

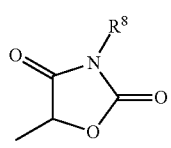

and R[8] is H or —(C$_1$-C$_4$)alkyl.

Another embodiment is a compound of Formula Ib where R is

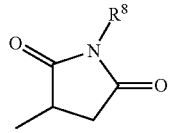

and R[8] is H or —(C$_1$-C$_4$)alkyl.

Another embodiment is a compound of Formula Ib where R is

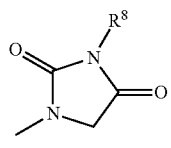

and R[8] is H or —(C$_1$-C$_4$)alkyl.

Another embodiment is a compound of Formula Ib where R is

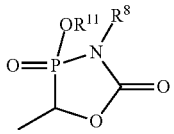

R⁸ is H or —(C₁-C₄)alkyl and R¹¹ is R⁸ is H or —(C₁-C₄)alkyl.

Another embodiment is a compound of Formula Ib where R is

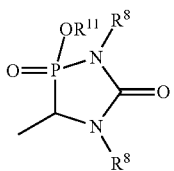

R⁸ is independently H or —(C₁-C₄)alkyl and R¹¹ is R⁸ is H or —(C₁-C₄)alkyl.

Another embodiment is a compound of Formula Ib where R is

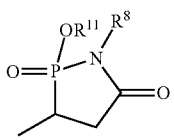

R⁸ is H or —(C₁-C₄)alkyl and R¹¹ is R⁸ is H or —(C₁-C₄)alkyl.

Another embodiment is a compound of Formula Ib where R is

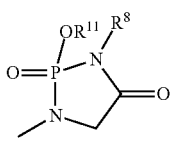

R⁸ is H or —(C₁-C₄)alkyl and R¹¹ is R⁸ is H or —(C₁-C₄)alkyl.

Another embodiment is a compound of Formula Ib where R is tetrazolyl.

Another embodiment is a compound of Formula Ib where L is —O—.

Another embodiment is a compound of Formula Ib where L is —N(R³)— and R³ is H or (C₁-C₄)alkyl or halo-(C₁-C₄)-alkyl.

Another embodiment is a compound of Formula Ib where R² is absent or R² is H, haloalkyl (e.g., trifluoromethyl) or halo.

Another embodiment of the present invention is a compound of Formula Ia of the formula Ia-1

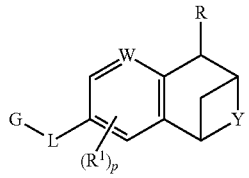

or a pharmaceutically acceptable ester, salt, solvate or prodrug thereof wherein G is aryl, arylalkyl, heteroaryl, or heteroarylalkyl, which is optionally substituted by at least one R²;

L is —O—, —C(O)—, —S(O)$_q$—, or —N(R³)—;

W is —C— or —N—;

Y is a bond, —[C(Rᵃ)(Rᵇ)]$_n$—O—[C(Rᵃ)(Rᵇ)]$_n$, —[C(Rᵃ)(Rᵇ)]$_n$—C(O)—[C(Rᵃ)(Rᵇ)]$_n$, —[C(Rᵃ)(Rᵇ)]$_n$—S(O)$_q$—[C(Rᵃ)(Rᵇ)]$_n$, —[C(Rᵃ)(Rᵇ)]$_m$— or —N(R⁸)—;

R is a group selected from the group consisting of (i)

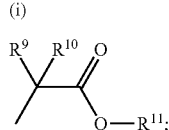

(ii)

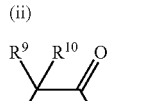

(iii)

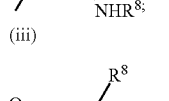

(iv)

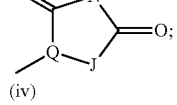

and (v) tetrazolyl, wherein

Q is —CH— or —N—, and

J is —S—, —CH₂—, —O— or —N(R⁸)—;

Rᵃ is independently selected from the group consisting of H, —OH, halo, alkoxy, alkyl, cycloalkyl, and cycloalkylalkyl;

Rᵇ is independently selected from the group consisting of H, —OH, halo, alkoxy, alkyl, cycloalkyl, and cycloalkylalkyl;

R¹ is independently selected from the group consisting of H, halogen, —SF₅, —S(O)$_q$-alkyl, —CN, —NO₂, —N(R⁶)(R⁷), —OH, alkyl, alkoxy, cycloalkyl, cycloalkyloxy, cycloalkylalkyl, and cycloalkylalkoxy wherein said alkyl, alkoxy, cycloalkly, cycloalkyloxy, cycloalkylalkyl, and cycloalkylalkoxy are optionally substituted with one or more groups selected from the group consisting of —OH, halo, —S(O)$_q$-alkyl, alkyl, haloalkyl, alkoxy, haloalkoxy, and cycloalkyl;

$R^2$ is independently selected from the group consisting of halogen, —SF$_5$, —CN, —NO$_2$, —N($R^6$)($R^7$), —OH, alkyl, alkoxy, cycloalkyl, cycloalkyloxy, cycloalkylalkyl, cycloalkylalkoxy, aryl, arylalkyl, heteroaryl, heteroarylalkyl and —S(O)$_q$-alkyl, wherein said alkyl, alkoxy, cycloalkyl, cycloalkyloxy, cycloalkylalkyl, cycloalkylalkoxy, aryl, arylalkyl, heteroaryl, and heteroarylalkyl are optionally substituted with one or more groups selected from the group consisting of —OH, halo, alkyl, —S(O)$_q$-alkyl, haloalkyl, alkoxy, haloalkoxy, and cycloalkyl;

$R^3$ is independently selected from the group consisting of H, alkyl, haloalkyl;

$R^4$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

$R^5$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

$R^6$ is independently selected from the group consisting of H, alkyl, cycloalkyl, cycloalkylalkyl, aryl, arylalkyl, heterocycloalkyl, heterocycloalkylalkyl, heteroaryl and heteroarylalkyl;

$R^7$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

or $R^6$ and $R^7$ together form a 4- to 7-membered heterocycloalkyl or a 5- or 5-membered heteroaryl ring optionally having, in addition to the N atom, 1 or 2 heteroatoms selected from the group consisting of O, N($R^8$), N or S, wherein said rings are optionally substituted by one or more $R^{12}$ moieties;

$R^8$ is independently selected from the group consisting of H, alkyl, cycloalkyl, cycloalkylalkyl, aryl, arylalkyl, heterocycloalkyl, heterocycloalkylalkyl, heteroaryl, heteroarylalkyl, —C(O)—$R^5$, —C(O)O—$R^5$, —C(O)N($R^6$)($R^7$), —C(O)-alkylene-O$R^4$, —C(O)-alkylene-N($R^6$)($R^7$), —C(O)-alkylene-S(O)$_q$—$R^5$, —S(O)$_q$—$R^5$, —S(O)$_q$-alkylene-O$R^4$, —S(O)$_q$-alkylene-N($R^6$)($R^7$), -alkylene-O$R^4$, -alkylene-S(O)$_q$—$R^5$, -alkylene-N($R^6$)($R^7$), and —S(O)$_2$N($R^6$)($R^7$) wherein said alkyl, cycloalkyl, cycloalkylalkyl, aryl, arylalkyl, heterocycloalkyl, heterocycloalkylalkyl, heteroaryl, heteroarylalkyl and alkylene are optionally substituted with one or more groups selected from the group consisting of —OH, halo, alkyl, haloalkyl, alkoxy, haloalkoxy and cycloalkyl;

$R^9$ is independently selected from the group consisting of H, alkyl, haloalkyl;

$R^{10}$ is independently selected from the group consisting of H, —OH, alkyl, alkyl, cycloalkyl or alkoxy wherein said alkyl, alkyl, cycloalkyl or alkoxy groups are optionally substituted with at least one substituent selected from the group consisting of halo and —O$R^5$;

$R^{11}$ is independently selected from the group consisting of H, alkyl, and haloalkyl;

wherein each of the alkyl, cycloalkyl, cycloalkylalkyl, aryl, arylalkyl, heterocycloalkyl, heterocycloalkylalkyl, heteroaryl, and heteroarylalkyl groups in $R^4$, $R^5$, $R^6$, and $R^7$ are independently unsubstituted or substituted by one or more $R^{12}$ groups, where $R^{12}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —O$R^4$, —C(O)—$R^5$, —C(O)O—$R^5$, —S(O)$_q$—$R^5$, —C(O)N($R^6$)($R^7$), and —S(O)$_2$N($R^6$)($R^7$), —NO$_2$, —SF$_5$, —CN, —N($R^6$)($R^7$) and halo and wherein each alkyl, cycloalkyl, cycloalkylalkyl, aryl, arylalkyl, heterocycloalkyl, heterocycloalkylalkyl, heteroaryl, and heteroarylalkyl group in $R^{12}$ is independently unsubstituted or substituted by one or more $R^{13}$ groups, where $R^{13}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —O$R^4$, —C(O)—$R^5$, —C(O)O—$R^5$, —S(O)$_q$—$R^5$, —C(O)N($R^6$)($R^7$), and —S(O)$_2$N($R^6$)($R^7$), —NO$_2$, —SF$_5$, —CN, and halo;

m is independently 1, 2, or 3;

n is independently 0, 1 or 2;

q is independently 0, 1, or 2; and p is 0, 1, 2, or 3.

An embodiment of the present invention is a compound of Formula Ia-1 where W is —CH—.

Another embodiment is a compound of Formula Ia-1 where Y is a bond.

Another embodiment is a compound of Formula Ia-1 where Y is —CH$_2$—.

Another embodiment is a compound of Formula Ia-1 where Y is —CH$_2$—CH$_2$—.

Another embodiment is a compound of Formula Ia-1 where W is —CH— and $R^3$ is halogen, cyano or —SF$_5$ and p is 1.

Another embodiment is a compound of Formula Ia-1 where G is aryl; for example, phenyl or naphthyl.

Another embodiment is a compound of Formula Ia-1 where G is heteroaryl; for example, pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, benzofurazanyl, indolyl, azaindolyl, benzimidazolyl, benzothienyl, quinolinyl, imidazolyl, thienopyridyl, quinazolinyl, thienopyrimidyl, isoquinolinyl, benzoazaindolyl, 1,2,4-triazinyl, benzothiazolyl.

Another embodiment is a compound of Formula Ia-1 where G is phenyl or naphthyl and $R^2$ is absent.

Another embodiment is a compound of Formula Ia-1 where G is phenyl or naphthyl that is sububstituted by one or two $R^2$ groups, which independently are haloalkyl (e.g., triflourormethyl), —SF$_5$, cyano or halo (e.g., fluoro or chloro).

Another embodiment is a compound of Formula Ia-1 where G is pyrimidinyl, pyridyl, or thiazolyl and $R^2$ is absent.

Another embodiment is a compound of Formula Ia-1 where G is pyrimidinyl, pyridyl, or thiazolyl that is substituted by one or two $R^2$ groups, which independently are $R^2$ is haloalkyl (e.g., trifluorormethyl), —SF$_5$, cyano or halo (e.g., fluoro or chloro).

Another embodiment is a compound of Formula Ia-1 where R is —CH$_2$—C(O)—OH.

Another embodiment is a compound of Formula Ia-1 where R is —CH$_2$—C(O)—O(C$_1$-C$_4$)alkyl.

Another embodiment is a compound of Formula Ia-1 where R is —CH$_2$—C(O)—NH$_2$.

Another embodiment is a compound of Formula Ia-1 where R is

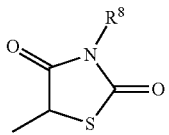

and R⁸ is H or —($C_1$-$C_4$)alkyl.

Another embodiment is a compound of Formula Ia-1 where R is

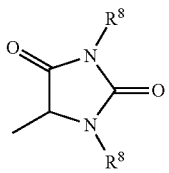

and R⁸ is independently H or —($C_1$-$C_4$)alkyl.

Another embodiment is a compound of Formula Ia-1 where R is

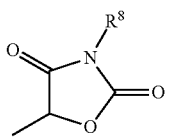

and R⁸ is H or —($C_1$-$C_4$)alkyl.

Another embodiment is a compound of Formula Ia-1 where R is

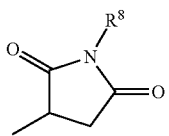

and R⁸ is H or —($C_1$-$C_4$)alkyl.

Another embodiment is a compound of Formula Ia-1 where R is

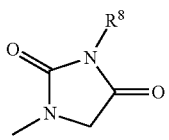

and R⁸ is H or —($C_1$-$C_4$)alkyl.

Another embodiment is a compound of Formula Ia-1 where L is —O—.

Another embodiment is a compound of Formula Ia-1 where L is —N(R³)— and R³ is H or ($C_1$-$C_4$)alkyl or halo-($C_1$-$C_4$)-alkyl.

Another embodiment is a compound of Formula Ia-1 where R² is absent or R² is H, haloalkyl (e.g., trifluoromethyl) or halo.

Another embodiment is a compound of Formula Ia of the formula

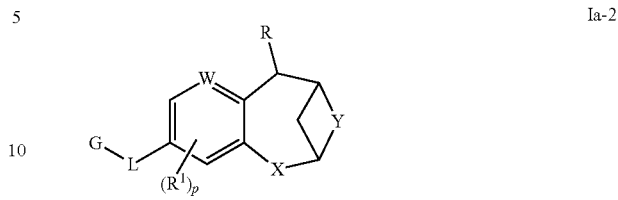

or a pharmaceutically acceptable ester, salt, solvate or prodrug thereof wherein
G is aryl, aryl alkyl, heteroaryl, or heteroarylalkyl, which is optionally substituted by at least one R²;
L is —O—, —C(O)—, —S(O)$_q$—, or —N(R³)—;
W is —C— or —N—;
X is a bond, —O—, —C(O)—, —S(O)$_q$, —C(R$^a$)(R$^b$)— or —N(R⁸)—;
Y is a bond, —[C(R$^a$)(R$^b$)]$_n$—O—[C(R$^a$)(R$^b$)]$_n$, —[C(R$^a$)(R$^b$)]$_n$—C(O)—[C(R$^a$)(R$^b$)]$_n$, —[C(R$^a$)(R$^b$)]$_n$—S(O)$_q$—[C(R$^a$)(R$^b$)]$_n$, —[C(R$^a$)(R$^b$)]$_m$— or —N(R⁸)—;
R is a group selected from the group consisting of (i)

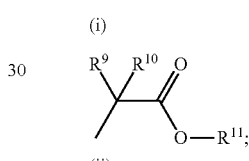

(ii)

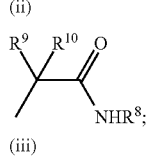

(iii)

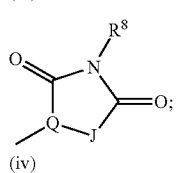

(iv)

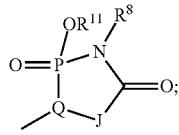

and
(v) tetrazolyl,
wherein
Q is —CH— or —N—, and
J is —S—, —CH₂—, —O— or —N(R⁸)—;
R$^a$ is independently selected from the group consisting of H, —OH, halo, alkoxy, alkyl, cycloalkyl, and cycloalkylalkyl;
R$^b$ is independently selected from the group consisting of H, —OH, halo, alkoxy, alkyl, cycloalkyl, and cycloalkylalkyl;
R¹ is independently selected from the group consisting of H, halogen, —SF₅, —S(O)$_q$-alkyl, —CN, —NO₂, —N(R⁶)(R⁷), —OH, alkyl, alkoxy, cycloalkyl, cycloalkyloxy, cycloalkylalkyl, and cycloalkylalkoxy wherein said alkyl, alkoxy, cycloalkyl, cycloalkyloxy, cycloalkylalkyl, and cycloalkylalkoxy are optionally substituted with one or more groups selected from the group consisting of —OH, halo, —S(O)$_q$-alkyl, alkyl, haloalkyl, alkoxy, haloalkoxy, and cycloalkyl;

$R^2$ is independently selected from the group consisting of halogen, —SF$_5$, —CN, —NO$_2$, —N(R$^6$)(R$^7$), —OH, alkyl, alkoxy, cycloalkyl, cycloalkyloxy, cycloalkylalkyl, cycloalkylalkoxy, aryl, arylalkyl, heteroaryl, heteroarylalkyl and —S(O)$_q$-alkyl, wherein said alkyl, alkoxy, cycloalkyl, cycloalkyloxy, cycloalkylalkyl, cycloalkylalkoxy aryl, arylalkyl, heteroaryl, and heteroarylalkyl are optionally substituted with one or more groups selected from the group consisting of —OH, halo, alkyl, —S(O)$_q$-alkyl, haloalkyl, alkoxy, haloalkoxy, and cycloalkyl;

$R^3$ is independently selected from the group consisting of H, alkyl, haloalkyl;

$R^4$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

$R^5$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

$R^6$ is independently selected from the group consisting of H, alkyl, cycloalkyl, cycloalkylalkyl, aryl, arylalkyl, heterocycloalkyl, heterocycloalkylalkyl, heteroaryl and heteroarylalkyl;

$R^7$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

or $R^6$ and $R^7$ together form a 4- to 7-membered heterocycloalkyl or a 5- or 5-membered heteroaryl ring optionally having, in addition to the N atom, 1 or 2 heteroatoms selected from the group consisting of O, N(R$^8$), N or S, wherein said rings are optionally substituted by one or more R$^{12}$ moieties;

$R^8$ is independently selected from the group consisting of H, alkyl, cycloalkyl, cycloalkylalkyl, aryl, arylalkyl, heterocycloalkyl, heterocycloalkylalkyl, heteroaryl, heteroarylalkyl, —C(O)—R$^5$, —C(O)O—R$^5$, —C(O)N(R$^6$)(R$^7$), —C(O)-alkylene-OR$^4$, —C(O)-alkylene-N(R$^6$)(R$^7$), —C(O)-alkylene-S(O)$_q$—R$^5$, —S(O)$_q$—R$^5$, —S(O)$_q$-alkylene-OR$^4$, —S(O)$_q$-alkylene-N(R$^6$)(R$^7$), -alkylene-OR$^4$, -alkylene-S(O)$_q$—R$^5$, -alkylene-N(R$^6$)(R$^7$), and —S(O)$_2$N(R$^6$)(R$^7$) wherein said alkyl, cycloalkyl, cycloalkylalkyl, aryl, arylalkyl, heterocycloalkyl, heterocycloalkylalkyl, heteroaryl, heteroarylalkyl and alkylene are optionally substituted with one or more groups selected from the group consisting of —OH, halo, alkyl, haloalkyl, alkoxy, haloalkoxy and cycloalkyl;

$R^9$ is independently selected from the group consisting of H, alkyl, haloalkyl;

$R^{10}$ is independently selected from the group consisting of H, —OH, alkyl, alkyl, cycloalkyl or alkoxy wherein said alkyl, alkyl, cycloalkyl or alkoxy groups are optionally substituted with at least one substituent selected from the group consisting of halo and —OR$^5$;

$R^{11}$ is independently selected from the group consisting of H, alkyl, and haloalkyl;

wherein each of the alkyl, cycloalkyl, cycloalkylalkyl, aryl, arylalkyl, heterocycloalkyl, heterocycloalkylalkyl, heteroaryl, and heteroarylalkyl groups in R$^4$, R$^5$, R$^6$, and R$^7$ are independently unsubstituted or substituted by one or more R$^{12}$ groups, where $R^{12}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —C(O)N(R$^6$)(R$^7$), and —S(O)$_2$N(R$^6$)(R$^7$), —NO$_2$, —SF$_5$, —CN, —N(R$^6$)(R$^7$) and halo and wherein each alkyl, cycloalkyl, cycloalkylalkyl, aryl, arylalkyl, heterocycloalkyl, heterocycloalkylalkyl, heteroaryl, and heteroarylalkyl group in R$^{12}$ is independently unsubstituted or substituted by one or more R$^{13}$ groups, where $R^{13}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —C(O)N(R$^6$)(R$^7$), and —S(O)$_2$N(R$^6$)(R$^7$), —NO$_2$, —SF$_5$, —CN, and halo;

m is independently 1, 2, or 3;

n is independently 0, 1 or 2;

q is independently 0, 1, or 2; and p is 0, 1, 2, or 3.

An embodiment of the present invention is a compound of Formula Ia-2 where W is —CH—.

Another embodiment is a compound of Formula Ia-2 where X is a bond.

Another embodiment is a compound of Formula Ia-2 where X is —CH$_2$—.

Another embodiment is a compound of Formula Ia-2 where X is —O—.

Another embodiment is a compound of Formula Ia-2 where Y is a bond.

Another embodiment is a compound of Formula Ia-2 where Y is —CH$_2$—.

Another embodiment is a compound of Formula Ia-2 where Y is —CH$_2$—CH$_2$—.

Another embodiment is a compound of Formula Ia-2 where W is —CH— and R$^3$ is halogen, cyano or —SF$_5$ and p is 1.

Another embodiment is a compound of Formula Ia-2 where G is aryl; for example, phenyl or naphthyl.

Another embodiment is a compound of Formula Ia-2 where G is heteroaryl; for example, pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, benzofurazanyl, indolyl, azaindolyl, benzimidazolyl, benzothienyl, quinolinyl, imidazolyl, thienopyridyl, quinazolinyl, thienopyrimidyl, isoquinolinyl, benzoazaindolyl, 1,2,4-triazinyl, benzothiazolyl.

Another embodiment is a compound of Formula Ia-2 where G is phenyl or naphthyl and R$^2$ is absent.

Another embodiment is a compound of Formula Ia-2 where G is phenyl or naphthyl that is sububstituted by one or two R$^2$ groups, which independently are haloalkyl (e.g., trifluorormethyl), —SF$_5$, cyano or halo (e.g., fluoro or chloro).

Another embodiment is a compound of Formula Ia-2 where G is pyrimidinyl, pyridyl, or thiazolyl and R$^2$ is absent.

Another embodiment is a compound of Formula Ia-2 where G is pyrimidinyl, pyridyl, or thiazolyl that is substituted by one or two R$^2$ groups, which independently are haloalkyl (e.g., trifluorormethyl), —SF$_5$, cyano or halo (e.g., fluoro or chloro).

Another embodiment is a compound of Formula Ia-2 where R is —CH$_2$—C(O)—OH.

Another embodiment is a compound of Formula Ia-2 where R is —CH$_2$—C(O)—O(C$_1$-C$_4$)alkyl.

Another embodiment is a compound of Formula Ia-2 where R is —CH$_2$—C(O)—NH$_2$.

Another embodiment is a compound of Formula Ia-2 where R is

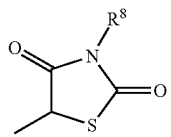

and R$^8$ is H or —(C$_1$-C$_4$)alkyl.

Another embodiment is a compound of Formula Ia-2 where R is

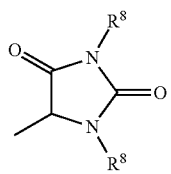

and R$^8$ is independently H or —(C$_1$-C$_4$)alkyl.

Another embodiment is a compound of Formula Ia-2 where R is

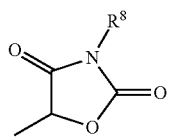

and R$^8$ is H or —(C$_1$-C$_4$)alkyl.

Another embodiment is a compound of Formula Ia-2 where R is

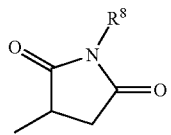

and R$^8$ is H or —(C$_1$-C$_4$)alkyl.

Another embodiment is a compound of Formula Ia-2 where R is

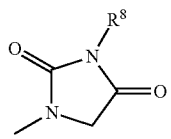

and R$^8$ is H or —(C$_1$-C$_4$)alkyl.

Another embodiment is a compound of Formula Ia-2 where L is —O—.

Another embodiment is a compound of Formula Ia-2 where L is —N(R$^3$)— and R$^3$ is H or (C$_1$-C$_4$)alkyl or halo-(C$_1$-C$_4$)-alkyl.

Another embodiment is a compound of Formula Ia-2 where R$^2$ is absent or R$^2$ is haloalkyl (e.g., trifluoromethyl) or halo.

Another embodiment of the present invention is a compound of Formula Ib

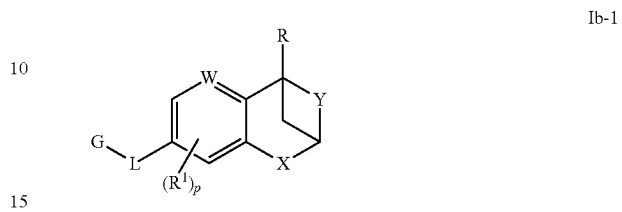

Ib-1 or a pharmaceutically acceptable ester, salt, solvate or prodrug thereof wherein G is aryl, aryl alkyl, heteroaryl, or heteroarylalkyl, which is optionally substituted by at least one R$^2$;

L is —O—, —C(O)—, —S(O)$_q$—, or —N(R$^3$)—;

W is —C— or —N—;

X is a bond, —O—, —C(O)—, —S(O)$_q$, —C(R$^a$)(R$^b$)— or —N(R$^8$)—;

Y is a bond, —[C(R$^a$)(R$^b$)]$_n$—O—[C(R$^a$)(R$^b$)]$_n$, —[C(R$^a$)(R$^b$)]$_n$—C(O)—[C(R$^a$)(R$^b$)]$_n$, —[C(R$^a$)(R$^b$)]$_n$—S(O)$_q$—[C(R$^a$)(R$^b$)]$_n$, —[C(R$^a$)(R$^b$)]$_m$— or —N(R$^8$)—;

R is a group selected from the group consisting of (i)

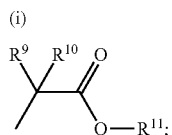

(ii)

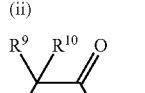

(iii)

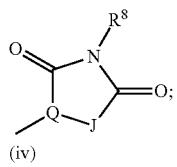

(iv)

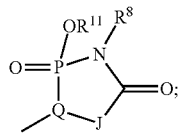

and (v) tetrazolyl wherein

Q is —CH— or —N—, and

J is —S—, —CH$_2$—, —O— or —N(R$^8$)—;

R$^a$ is independently selected from the group consisting of H, —OH, halo, alkoxy, alkyl, cycloalkyl, and cycloalkylalkyl;

R$^b$ is independently selected from the group consisting of H, —OH, halo, alkoxy, alkyl, cycloalkyl, and cycloalkylalkyl;

$R^1$ is independently selected from the group consisting of H, halogen, —SF$_5$, —S(O)$_q$-alkyl, —CN, —NO$_2$, —N(R$^6$)(R$^7$), —OH, alkyl, alkoxy, cycloalkyl, cycloalkyloxy, cycloalkylalkyl, and cycloalkylalkoxy wherein said alkyl, alkoxy, cycloalkylalkoxy, cycloalkylalkyl, and cycloalkylalkoxy are optionally substituted with one or more groups selected from the group consisting of —OH, halo, —S(O)$_q$-alkyl, alkyl, haloalkyl, alkoxy, haloalkoxy, and cycloalkyl;

$R^2$ is independently selected from the group consisting of halogen, —SF$_5$, —CN, —NO$_2$, —N(R$^6$)(R$^7$), —OH, alkyl, alkoxy, cycloalkyl, cycloalkyloxy, cycloalkylalkyl, cycloalkylalkoxy, aryl, arylalkyl, heteroaryl, heteroarylalkyl and —S(O)$_q$-alkyl, wherein said alkyl, alkoxy, cycloalkyl, cycloalkyloxy, cycloalkylalkyl, cycloalkylalkoxy, aryl, arylalkyl, heteroaryl, and heteroarylalkyl are optionally substituted with one or more groups selected from the group consisting of —OH, halo, alkyl, —S(O)$_q$-alkyl, haloalkyl, alkoxy, haloalkoxy, and cycloalkyl;

$R^3$ independently selected from the group consisting of H, alkyl, haloalkyl;

$R^4$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

$R^5$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

$R^6$ is independently selected from the group consisting of H, alkyl, cycloalkyl, cycloalkylalkyl, aryl, arylalkyl, heterocycloalkyl, heterocycloalkylalkyl, heteroaryl and heteroarylalkyl;

$R^7$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

or $R^6$ and $R^7$ together form a 4- to 7-membered heterocycloalkyl or a 5- or 5-membered heteroaryl ring optionally having, in addition to the N atom, 1 or 2 heteroatoms selected from the group consisting of O, N(R$^8$), N or S, wherein said rings are optionally substituted by one or more R$^{12}$ moieties;

$R^8$ is independently selected from the group consisting of H, alkyl, cycloalkyl, cycloalkylalkyl, aryl, arylalkyl, heterocycloalkyl, heterocycloalkylalkyl, heteroaryl, heteroarylalkyl, —C(O)—R$^5$, —C(O)O—R$^5$, —C(O)N(R$^6$)(R$^7$), —C(O)-alkylene-OR$^4$, —C(O)-alkylene-N(R$^6$)(R$^7$), —C(O)-alkylene-S(O)$_q$—R$^5$, —S(O)$_q$—R$^5$, —S(O)$_q$-alkylene-OR$^4$, —S(O)$_q$-alkylene-N(R$^6$)(R$^7$), -alkylene-OR$^4$, -alkylene-S(O)$_q$—R$^5$, -alkylene-N(R$^6$)(R$^7$), and —S(O)$_2$N(R$^6$)(R$^7$) wherein said alkyl, cycloalkyl, cycloalkylalkyl, aryl, arylalkyl, heterocycloalkyl, heterocycloalkylalkyl, heteroaryl, heteroarylalkyl and alkylene are optionally substituted with one or more groups selected from the group consisting of —OH, halo, alkyl, haloalkyl, alkoxy, haloalkoxy and cycloalkyl;

$R^9$ is independently selected from the group consisting of H, alkyl, haloalkyl;

$R^{10}$ is independently selected from the group consisting of H, —OH, alkyl, alkyl, cycloalkyl or alkoxy wherein said alkyl, alkyl, cycloalkyl or alkoxy groups are optionally substituted with at least one substituent selected from the group consisting of halo and —OR$^5$;

$R^{11}$ is independently selected from the group consisting of H, alkyl, and haloalkyl;

wherein each of the alkyl, cycloalkyl, cycloalkylalkyl, aryl, arylalkyl, heterocycloalkyl, heterocycloalkylalkyl, heteroaryl, and heteroarylalkyl groups in R$^4$, R$^5$, R$^6$, and R$^7$ are independently unsubstituted or substituted by one or more R$^{12}$ groups, where $R^{12}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —C(O)N(R$^6$)(R$^7$), and —S(O)$_2$N(R$^6$)(R$^7$), —NO$_2$, —SF$_5$, —CN, —N(R$^6$)(R$^7$) and halo and wherein each alkyl, cycloalkyl, cycloalkylalkyl, aryl, arylalkyl, heterocycloalkyl, heterocycloalkylalkyl, heteroaryl, and heteroarylalkyl group in R$^{12}$ is independently unsubstituted or substituted by one or more R$^{13}$ groups, where $R^{13}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —C(O)N(R$^6$)(R$^7$), and —S(O)$_2$N(R$^6$)(R$^7$), —NO$_2$, —SF$_5$, —CN, and halo;

m is independently 1, 2, or 3;
n is independently 0, 1 or 2;
q is independently 0, 1, or 2; and
p is 0, 1, 2, or 3.

An embodiment of the present invention is a compound of Formula Ib-1 where W is —CH—.

Another embodiment is a compound of Formula Ib-1 where X is a bond.

Another embodiment is a compound of Formula 1b-1 where X is —CH$_2$—.

Another embodiment is a compound of Formula Ib-1 where X is —O—.

Another embodiment is a compound of Formula Ib-1 where Y is a bond.

Another embodiment is a compound of Formula Ib-1 where Y is —CH$_2$—.

Another embodiment is a compound of Formula Ib-1 where Y is —CH$_2$—CH$_2$—.

Another embodiment is a compound of Formula Ib-1 where W is —CH— and R$^1$ is halogen, cyano or —SF$_5$ and p is 1.

Another embodiment is a compound of Formula Ib-1 where G is aryl; for example, phenyl or naphthyl.

Another embodiment is a compound of Formula Ib-1 where G is heteroaryl; for example, pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, benzofurazanyl, indolyl, azaindolyl, benzimidazolyl, benzothienyl, quinolinyl, imidazolyl, thienopyridyl, quinazolinyl, thienopyrimidyl, isoquinolinyl, benzoazaindolyl, 1,2,4-triazinyl, benzothiazolyl.

Another embodiment is a compound of Formula Ib-1 where G is phenyl or naphthyl and R$^2$ is absent.

Another embodiment is a compound of Formula Ib-1 where G is phenyl or naphthyl that is substituted by one or two R$^2$ groups, which independently are haloalkyl (e.g., trifluoromethyl), —SF$_5$, cyano or halo (e.g., fluoro or chloro).

Another embodiment is a compound of Formula Ib-1 where G is pyrimidinyl, pyridyl, or thiazolyl and R$^2$ is absent.

Another embodiment is a compound of Formula Ib-1 where G is pyrimidinyl, pyridyl, or thiazolyl that is substituted by one or two R² groups, which independently are haloalkyl (e.g., trifluorormethyl), —SF₅, cyano or halo (e.g., fluoro or chloro).

Another embodiment is a compound of Formula Ib-1 where R is —CH₂—C(O)—OH.

Another embodiment is a compound of Formula Ib-1 where R is —CH₂—C(O)—O(C₁-C₄)alkyl.

Another embodiment is a compound of Formula Ib-1 where R is —CH₂—C(O)—NH₂.

Another embodiment is a compound of Formula Ib-1 where R is

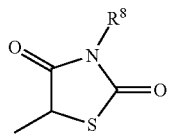

and R⁸ is H or —(C₁-C₄)alkyl.

Another embodiment is a compound of Formula Ib-1 where R is

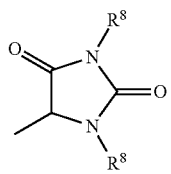

and R⁸ is independently H or —(C₁-C₄)alkyl.

Another embodiment is a compound of Formula Ib-1 where R is

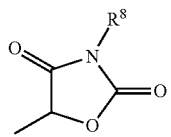

and R⁸ is H or —(C₁-C₄)alkyl.

Another embodiment is a compound of Formula Ib-1 where R is

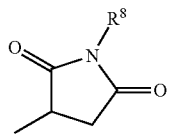

and R⁸ is H or —(C₁-C₄)alkyl.

Another embodiment is a compound of Formula Ib-1 where R is

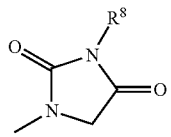

and R⁸ is H or —(C₁-C₄)alkyl.

Another embodiment is a compound of Formula Ib-1 where L is —O—.

Another embodiment is a compound of Formula Ib-1 where L is —N(R³)— and R³ is H or (C₁-C₄)alkyl or halo-(C₁-C₄)-alkyl.

Another embodiment is a compound of Formula Ib-1 where R² is absent or R² is haloalkyl (e.g., trifluoromethyl) or halo.

A further embodiment of the present invention is a compound selected from the group consisting of

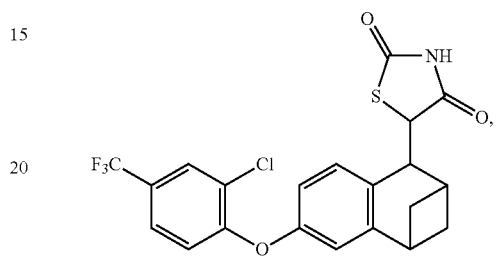

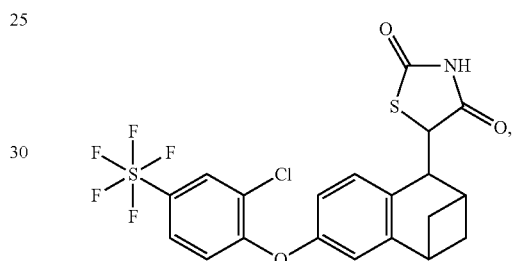

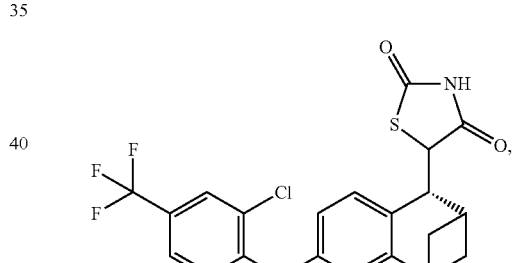

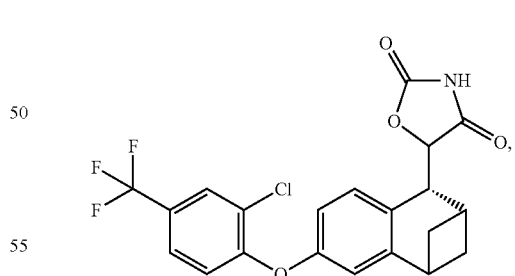

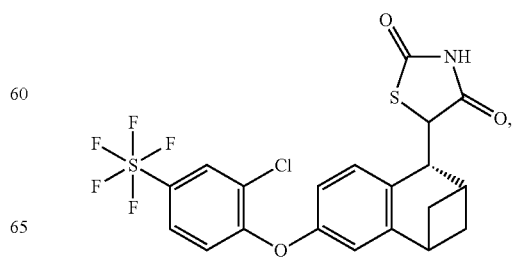

or a pharmaceutically acceptable ester, salt, or solvate thereof.

A further embodiment of the present invention is compounds of Formula I in isolated and purified form.

A further embodiment of the present invention is the use of a compound of Formula I or a pharmaceutically acceptable salt, ester, solvate or prodrug thereof in the manufacture of a medicament for the treatment of Type 2 diabetes mellitus.

A further embodiment of the present invention is the use of a compound of Formula I or a pharmaceutically acceptable salt, ester, solvate or prodrug thereof in the manufacture of a medicament for the treatment of diseases associated with Type 2 diabetes mellitus (for example, insulin resistance, obesity and lipid disorders).

A further embodiment of the present invention is the use of a compound of Formula I or a pharmaceutically acceptable salt, ester, solvate or prodrug thereof in the manufacture of a medicament for the treatment of Syndrome X.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkylene" means a dialent alkyl group; e.g —CH$_2$— (methylene) or —CH$_2$CH$_2$— (ethylene). The hydrogen groups may be replaced by one or more of the alkyl substituents defined for alkyl above.

"Aryl" means an aromatic monocyclic or multicyclic ring system, in which at least one of the multicyclic rings is an aryl ring, comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. Non-limiting examples of aryl multicyclic ring systems include:

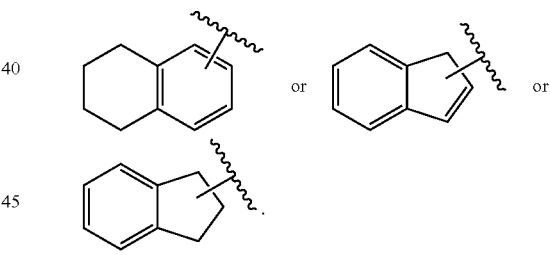

"Heteroaryl" means an aromatic monocyclic or multicyclic ring system, in which at least one of the multicyclic rings is aromatic, comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

Non-limiting examples of heteroaryl multicyclic ring systems include:

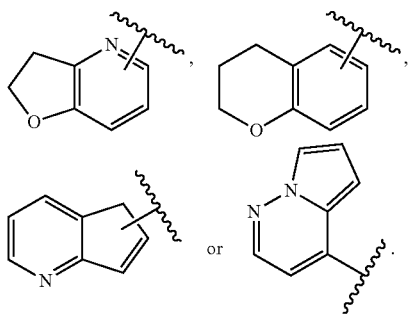

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl-alkyl-group in which the cycloalkyl and alkyl are as previously described. Preferred cycloalkylalkyls comprise a lower alkyl group.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Heterocycloalkyl" or "heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, imidazolidinyl, pyrazolidinyl and the like.

It should be noted that in saturated heterocyclyl containing systems of this invention, there are no hydroxyl, amino, or thiol groups on carbon atoms adjacent to a N, O or S atom. Thus, for example, in the ring:

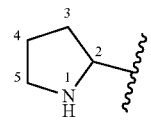

there is no —OH attached directly to carbons marked 2 and 5. It should also be noted that this definition does not preclude (=O), (=S), or (=N) substitutions, or their tautomeric forms, on C atoms adjacent to a N, O or S. Thus, for example, in the above ring, (=O) substitution on carbon 5, or its imino ether tautomer is allowed.

Non-limiting examples which illustrate the present invention are as follows:

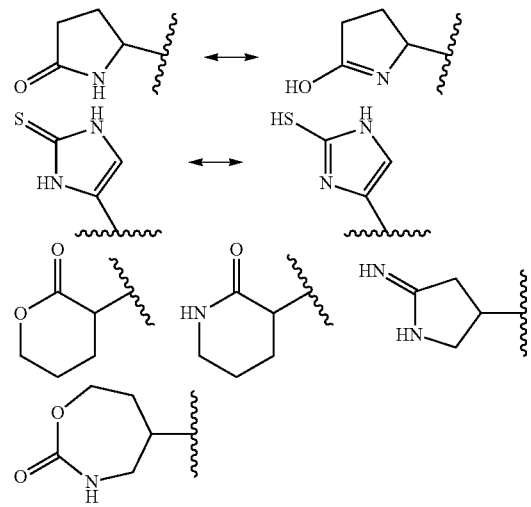

The following non-limiting examples serve to illustrate radicals not contemplated by the present invention:

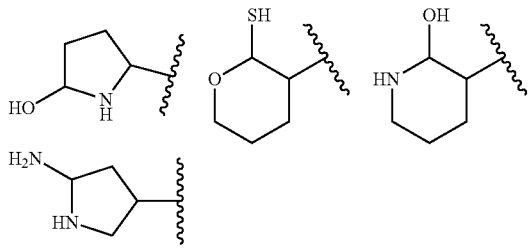

"Heteroarylalkyl" or "heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocycloalkylalkyl" means a heterocycloalkyl-alkyl group in which the heteroalkyl and the alkyl are as previously described. Preferred heterocyclylalkyls contain a lower alkyl group. Non-limiting examples of suitable heterocyclylalkyl groups include piperidylmethyl, piperidylethyl, pyrrolidylmethyl, morpholinylpropyl, piperazinylethyl, azindylmethyl, azetidylethyl, oxiranylpropyl and the like. The bond to the parent moiety is through the alkyl group.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C(O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Cycloalkoxy" means a cycloalkyl-O— group in which the cycloalkyl group is as previously described.

"Cycloalkylalkoxy" means a cycloalkylalkyl-O group in which the cycloalkylalkyl group is as previously described.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" or "arylalkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Heteroarylalkoxy" means a heteroarylalkyl-O-group in which the heteroarylalkyl group is as previously described.

"Heterocycloalkylalkoxy" means a heterocycloalkylalkyl-O group in which the hetrocycloalkylalkyl group is as previously described.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Heteroalkylthio" means a heteroalkyl-S— group in which the heteroalkyl group is a previously described.

"Heteroarylthio" means a heteroaryl-S— group in which the heteroaryl group is previously described.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

It is noted that carbons of formula I can be replaced with 1-3 silicon atoms, provided all valency requirements are satisfied.

The term "optionally substituted" means optional substitution with the specified groups, radicals or moieties.

The straight line ——— as a bond generally indicates a mixture of, or either of, the possible isomers, non-limiting example(s) include, containing (R)— and (S)-stereochemistry. For example,

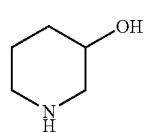

means containing both

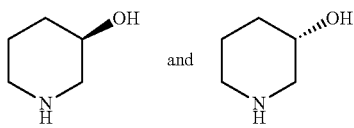 [SMILES: O[C@@H]1CCCNC1 ; O[C@H]1CCCNC1]

A dashed line (-----) represents an optional bond.
Lines drawn into the ring systems, such as, for example:

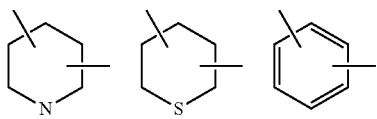

indicate that the indicated line (bond) may be attached to any of the substitutable ring atoms, non-limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

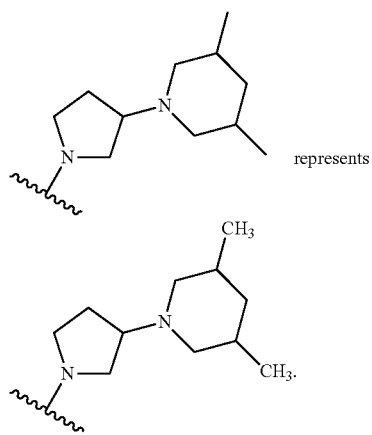

represents

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or formula, its definition on each occurrence is independent of its definition at every other occurrence.

Unless defined otherwise, all definitions for the variables follow the convention that the group to the right forms the point of attachement to the molecule; i.e., if a definition is arylalkyl, this means that the alkyl portion of the definition is attached to the molecule. Further, all divalent variable are attached from left to right.

As used herein, the term "composition" is intended to encompass a product comprising the specified ingredients in the specified amounts, as well as any product which results, directly or indirectly, from combination of the specified ingredients in the specified amounts.

In this application, unless otherwise indicated, whenever there is a structural formula provided, such as those of Formula I, this formula is intended to encompass all forms of a compound such as, for example, any solvates, hydrates, stereoisomers, tautomers, etc.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$alkyl, and the like.

Similarly, if a compound of Formula I contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of Formula I incorporates —NH— functional group, such as in a primary or secondary amine or in a nitrogen-containing heterocycle, such as imidazole or piperazine ring, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Metabolic conjugates, such as glucuronides and sulfates which can undergo reversible conversion to the compounds of Formula I are contemplated in the present invention.

"Effective amount" or "therapeutically effective amount" is meant to describe an amount of compound or a composition of the present invention effective in producing the desired therapeutic, ameliorative, inhibitory or preventative effect.

The terms "purified", "in purified form" or "in isolated and purified form," as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'Ideucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on its website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons or sulfurs on various substituents, including enantiomeric forms (which may exist even in the absence of asymmetric carbons), rotameric forms, atropisomers, and diastereomeric forms, are contemplated within the scope of this invention. For example, if a compound of Formula I incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

Polymorphic forms of the compounds of Formula I, and of the salts, solvates and prodrugs of the compounds of Formula I, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements)

and hence may be preferred in some circumstances. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

The compounds according to the invention have pharmacological properties; in particular, the compounds of Formula I can be useful as GPR 40 receptor agonists.

A preferred dosage is about 0.1 to 100 mg/kg of body weight/day of the compound of Formula I. An especially preferred dosage is about 0.1 to 30 mg/kg of body weight/day of a compound of Formula I, or a pharmaceutically acceptable salt or solvate of said compound.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

An aspect of this invention is that the pharmaceutical composition is in a solid dosage form comprising a compound of Formula I or a pharmaceutical acceptable salt, ester, solvate or prodrug thereof and a least one pharmaceutically acceptable carrier, adjuvant or vehicle.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 100 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 1000 mg/day, preferably from 1 mg/day to 100 mg/day, in one to four divided doses, or in a sustained release form.

Compounds of Formula I (including their pharmaceutically acceptable salts, esters, solvates and prodrugs) may be used in combination with other drugs that may also be useful in the treatment of amelioration of the diseases or conditions for which compounds of Formula I are useful. Such other drugs may be administered, by a route and in an amount commonly used therefor, contemporaneously or sequentially with a compound of Formula I. In the treatment of patients who have Type 2 diabetes, insulin resistance, obesity, lipid disorders, metabolic syndrome, and co-morbidities that accompany these diseases, more than one drug is commonly administered. The compounds of this invention may generally be administered to a patient who is already taking one or more other drugs for these conditions.

When a compound of Formula I (including their pharmaceutically acceptable salts, esters, solvates and prodrugs) is used contemporaneously with one or more other drugs, a pharmaceutical composition in unit dosage form containing such other drugs and the compounds of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound Formula I, and either administered separately or in the same pharmaceutical composition, include, but are not limited to:

(a) PPAR gamma agonists and selective PPAR gamma partial agonists (SPPARM's) including both glitazones and non-glitazones (e.g. troglitazone, pioglitazone, englitazone, MCC-555, rosiglitazone, balaglitazone, netoglitazone, T-131, LY-300512, and LY-818, and SPPARM's described in U.S. Pat. No. 6,525,083, WO 2004/020409, and WO 2004/020408);

(b) biguanides such as metformin and phenformin;

(c) protein tyrosine phosphatase-1B (PTP-1B) inhibitors;

(d) dipeptidyl peptidase IV (DP-IV) inhibitors, such as sitagliptin, saxagliptin, and vildagliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acy CoA:cholesterol acyltransferase (ACAT) inhibitors, such as avasimibe, (vii) CETP inhibitors, such as torcetrapib and compounds described in WO 2005/100298, WO 2006/014413, and WO 2006/014357, and (viii) phenolic anti-oxidants, such as probucol;

(i) PPAR α/γ dual agonists, such as muraglitazar, tesaglitazar, farglitazar, and JT-501;

(j) PPARδ agonists such as those disclosed in WO 97/28149;

(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and β₃ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1, (p) GIP-1, (q) GLP-1 analogs, such as exendins, for example exenatide (Byetta), (r) Glucokinase activators;

(s) GPR 119 agonists;

(t) GPR120 agonists; and (u) Hydroxysterol dehydrogenase-1 (HSD-1) inhibitors.

The above combinations include combinations of a compound of the present invention not only with one other active compounds, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Another aspect of this invention is a kit comprising a therapeutically effective amount of at least one compound of Formula I or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one therapeutic agent listed above, wherein the amounts of the two or more ingredients result in desired therapeutic effect.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be analyzed for their composition and purity as well as characterized by standard analytical techniques such as, for example, elemental anyalysis, NMR, mass spectroscopy and IR spectra.

One skilled in the art will recognize that reagents and solvents actually uised may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

Where NMR data are presented, $^1$H spectra were obtained on either a Varian VXR-200 (200 MHz, $^1$H), Varian Gemini-300 (300 MHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The invention disclosed herein is exemplified by the following illustrative processes which should not be construed to limit the scope of the disclosure. Alternative mechanistic pathways and analogous structures will be apparent to those skilled in the art.

The invention disclosed herein is exemplified by the following illustrative processes which should not be construed to limit the scope of the disclosure. Alternative mechanistic pathways and analogous structures will be apparent to those skilled in the art.

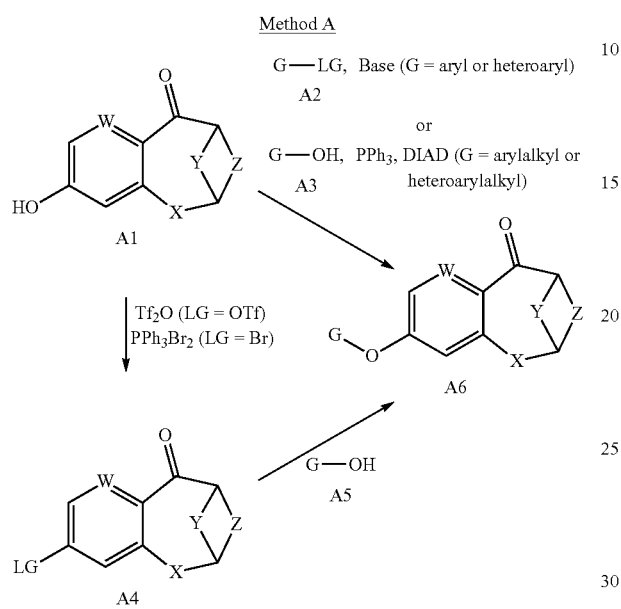

Method A describes general methods towards the preparation of compounds of formula (I) that relies on the formation of ketone intermediate A6. One way to prepare intermediate A6 is via coupling phenol ketone intermediate A1 with A2 (where LG is a leaving group such as halo or triflate and G is aryl or heteroaryl) under SNAr conditions using a base such as cesium carbonate. Another way to prepare A6 is to couple intermediate A1 with alcohol A3 (where G is arylalkyl or heteroarylalkyl) under Mitsunobu conditions such as with triphenylphosphine and diisopropyl azodicarboxylate. An alternate way to generate A6 is to couple activated aryl ketone A4 (where LG is a leaving group such as halo or triflate) with alcohol or phenol-like A5 under SNAr conditions in the presence of a base such as cesium carbonate. A4 can be generated from A1 when desirable, via condensation with triflic anhydride for LG=triflate, or via halogenation with triphenylphosphine and bromine for LG=bromine.

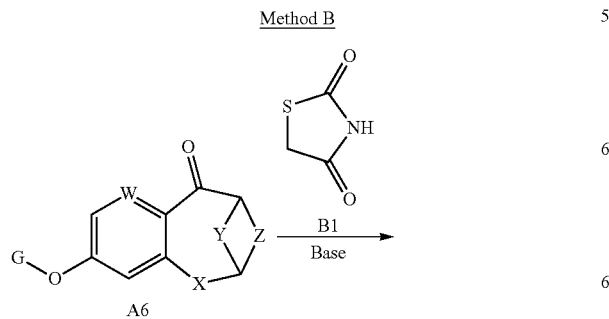

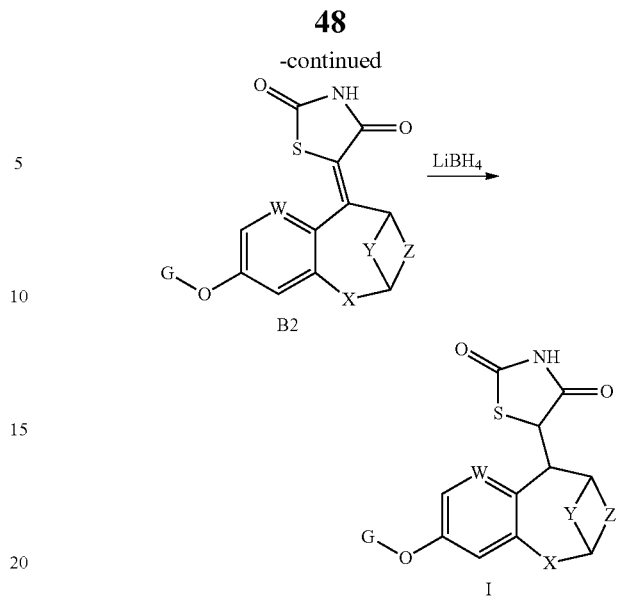

Method B describes one general method to convert intermediate A6 into a compound of formula (I). Ketone intermediate A6 is reacted with 2,4-thiazolidine dione B1 in the presence of a base such as sodium acetate to produce intermediate B2. A2 is then reduced with a reducing agent such as lithium borohydride to give the compound of formula (I) as a mixture of diastereoisomers. Those diastereoisomers can be optionally separated via chiral purification, resolution or via any method known to one skilled in the art. A2 may also be reduced under asymmetric reduction conditions to generate the compound of formula (I) as an optically enriched compound.

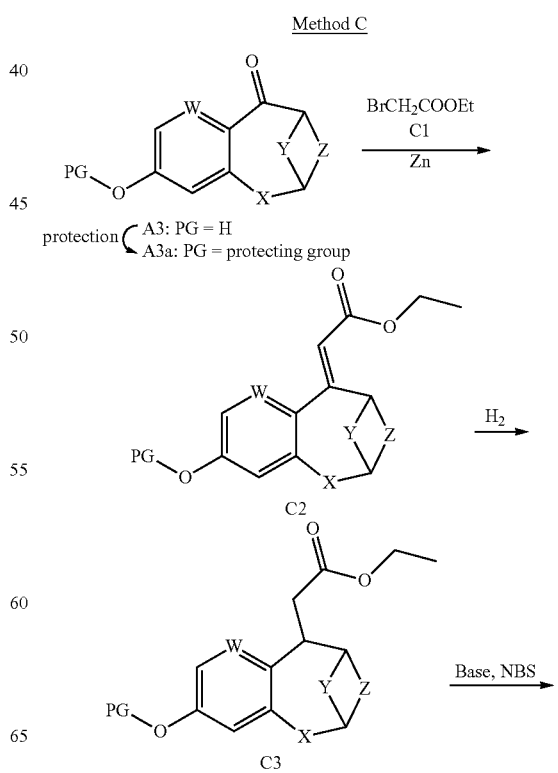

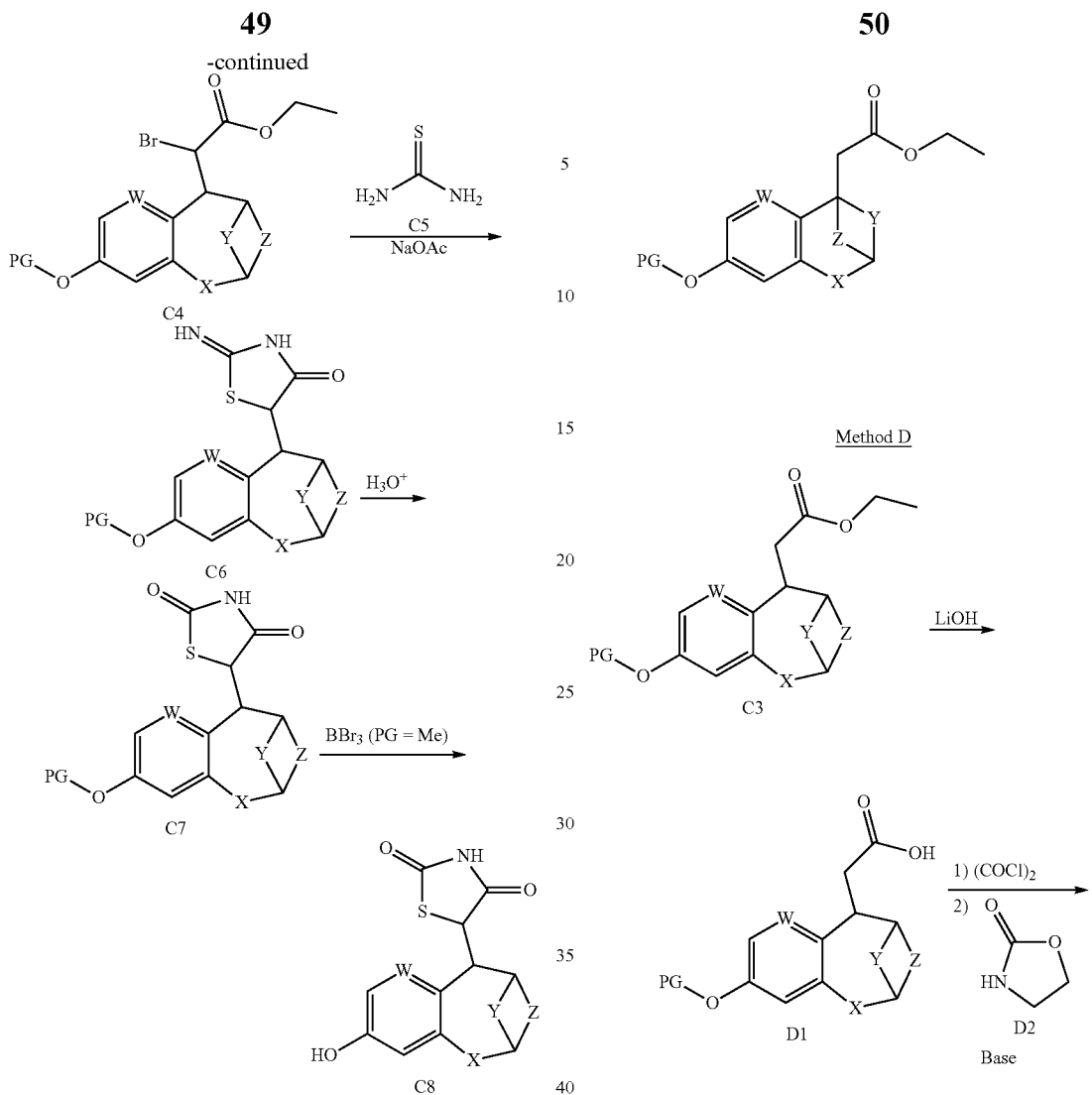

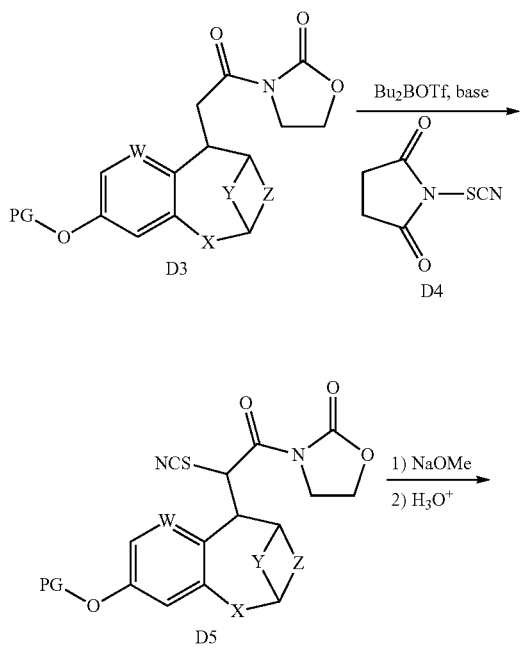

Method C is a general alternate method for compounds of formula (I) that relies on the formation of intermediate C8. Intermediate A3 is first protected at the phenol into intermediate A3a by using standard phenol protection methodology such as reaction with iodomethane when PG=methyl. Intermediate A3-p is then subjected to Reformatsky conditions, such as zinc and ethyl bromoacetate C1 or an equivalent, to provide C2. Intermediate C2 is reduced, optionally under asymmetric reduction conditions, to generate intermediate C3 as an optically enriched compound or as a mixture of diastereoisomers that can be optionally purified via chiral purification, resolution or via any method known to one skilled in the art. C3 is bromated under general bromination conditions such as treatment with N-bromosuccinimide and a base such as LHMDS to provide intermediate C4. The 2,4-thiazolidine dione ring is then installed through treatment of C4 with thiourea C5 (producing C6) followed by hydrolysis to give C7. Removal of the protection group in C7, for example with boron tribromide when PG=methyl, results in intermediate C8. Partial variation around Method C may also be apparent to those skilled in the art, for example by using an alternate intermediate C3

51

-continued

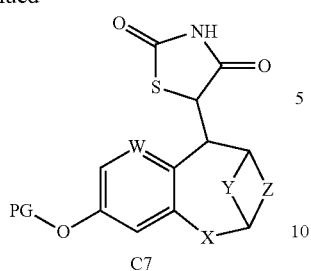
C7

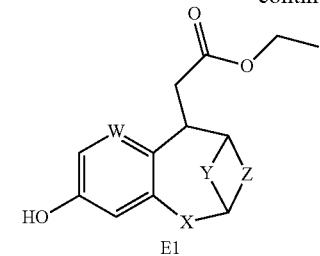
E1

Method D is a general alternate method for the preparation of intermediate C7 that uses conditions similar to the ones described by Falck, J. R. et al. *Bioorg. Med. Chem. Lett.* 2008, 18, 1768. Intermediate C3 is hydrolyzed in the presence of a base such as lithium hydroxide to generate acid D1 which can be optionally optically enriched via chiral purification, resolution (for example with a chiral salt or chiral amine) or via any method known to one skilled in the art. D1 is then converted into an acyl chloride with a reagent such as oxalyl chloride and then reacted with 2-oxazolidinone D2 to give intermediate D3. D3 is in turn converted into thiocyanato intermediate D5 via the formation of an enol boronate with di-n-butylboron triflate and diisopropylamine for example, followed by treatment with N-thiocyanatosuccinimide D4. The 2,4-thiazolidine dione ring is then installed via treatment of D5 with a base such as sodium methoxide followed by hydrolysis to give C7. Alternate strategies using a chiral oxazolidinone instead of D2 to allow for the separation of D1 enantiomers as in WO 2006/083612 may be envioned for those skilled in the art. Such strategies may generate optically enriched or optically pure C7 following the sodium methoxide and hydrolysis treatment. Variation of Method D may also be apparent to those skilled in the art, for example by using an alternate intermediate C3 such as:

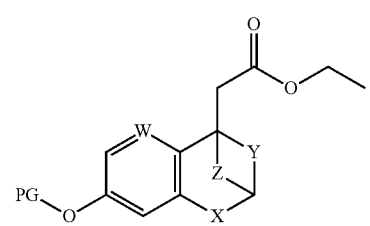

Method E

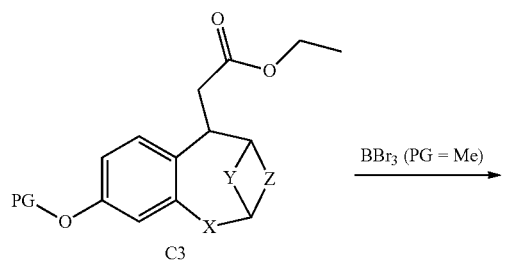
C3

52

-continued

G—LG,
A2
Base (G = aryl or heteroaryl)

or

G—OH,
A3
PPh₃, DIAD (G = arylalkyl or heteroarylalkyl)

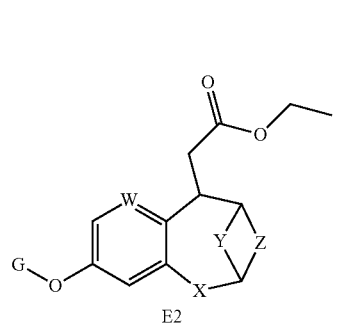
E2

Method C from C3 to C7
or
Method D

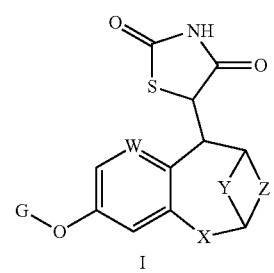
I

Method E is a general alternate method that utilizes processes described in Methods A, C and D. Following the deprotection of the protecting group in intermediate C3, for example with boron tribromide for PG=methyl, the resulting phenol E1 is converted into intermediate E2 using any of the processes described in Method A, then E2 is reacted using steps C3 to C7 of Method C, or the steps in method D, to give the compound of formula (I) as an optically enriched compound or as a mixture of diastereoisomers that can be optionally separated via chiral purification, resolution or via any method known to one skilled in the art. Variation of Method E may also be apparent to those skilled in the art, for example by using an alternate intermediate C3 such as:

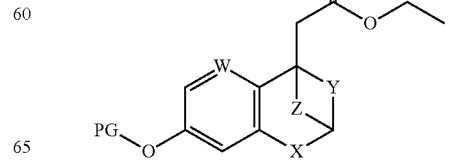

Method F

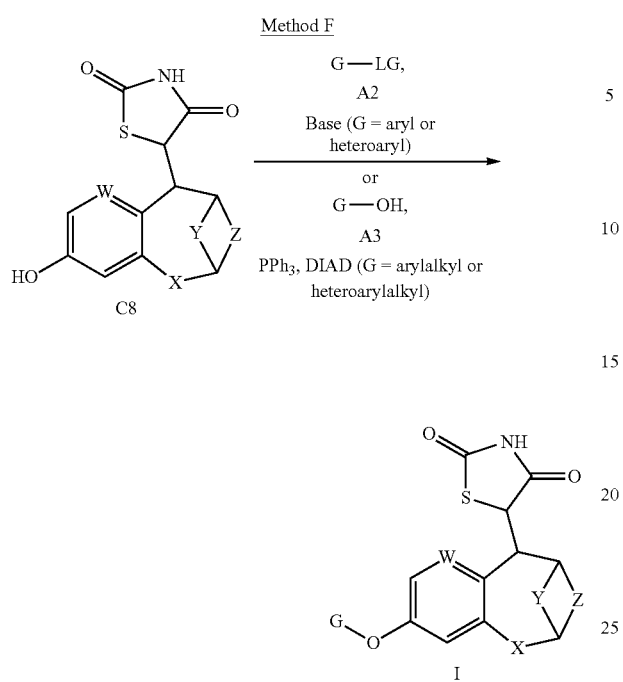

Method F is a general alternate method that utilizes any of the processes described in Method A, as well as alternate conditions known to one skilled in the art, to convert intermediate C8 into the compound of formula (I) as an optically enriched compound or as a mixture of diastereoisomers that can be optionally separated via chiral purification, resolution or via any method known to one skilled in the art. Variation of Method F may also be apparent to those skilled in the art, for example by using an alternate intermediate C8 such as:

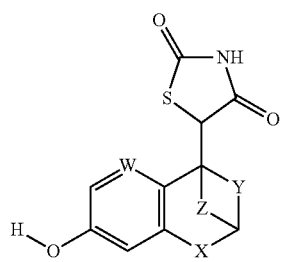

Method G

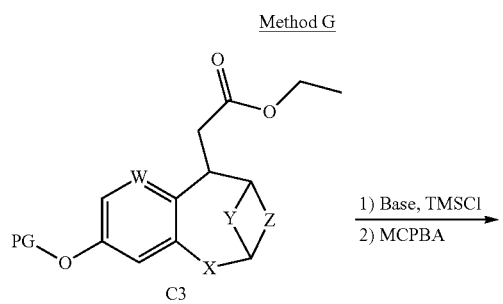

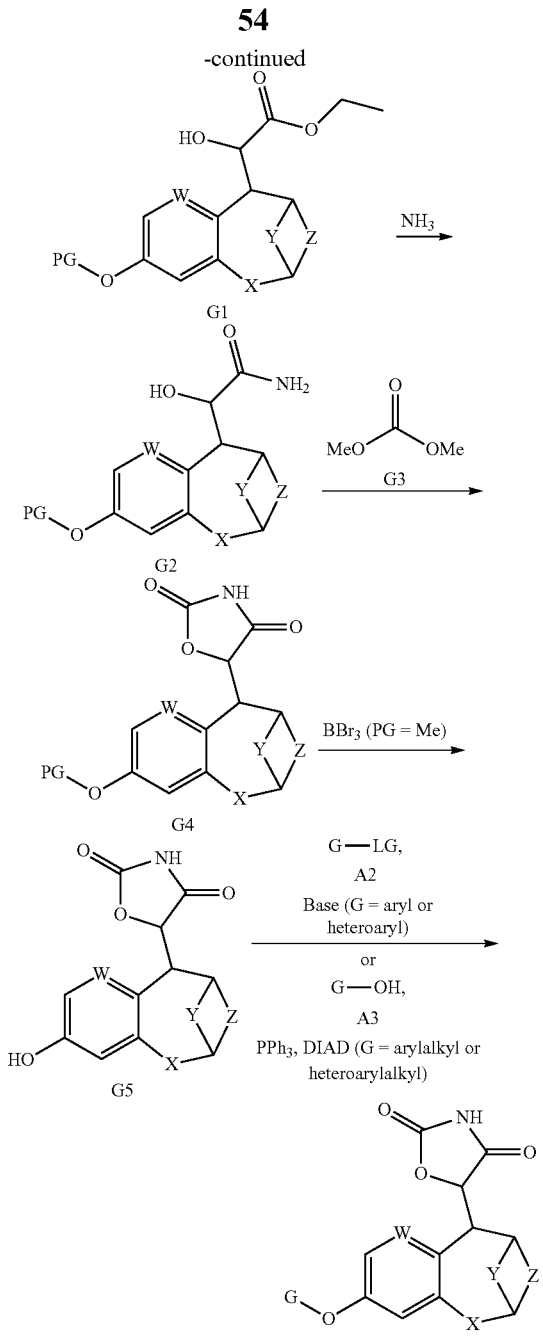

Method G is a general alternate method for the introduction of 2,4-oxadiazolidine dione instead of the 2,4-thiodiazolidine dione that utilizes alpha-hydroxylation of the intermediate C3 using conditions similar to the ones described by Rubottom, G. M. et al. *Synth. Commun.* 1981, 11, 505. In this method, C3 is treated with a base such as NaHMDS followed by trimethylsilyl chloride and the resulting ketene acetal intermediate is trapped with MCPBA followed by treatment with TBAF to give G1. G1 is reacted with ammonia to yield the hydroxyamide G2. G2 is in turn converted into 2,4-oxazolidine dione G4 through treatment with dimethylcarbonate G3. Following the deprotection of the protecting group in G4, for example with boron tribromide for PG=methyl, the resulting phenol G5 undergoes any of the processes described in Method A, as well as alternate conditions known to one skilled in the art, to give the compound of formula (I) as an optically enriched compound or as a mixture of diastereoisomers that can be optionally separated via chiral purification, resolution or via any method known to one skilled in the art. Variation of Method G may also be apparent to those skilled in the art, for example by using an alternate intermediate C3 such as:

to give the compound of formula (I) as an optically enriched compound or as a mixture of diastereoisomers that can be optionally separated via chiral purification, resolution or via any method known to one skilled in the art. As an alternate variation, the alpha-hydroxyl group in G1 may be protected with tert-butylchlorodiphenylsilane prior to the sequence of steps described in Method H scheme. After hydrolysis with lithium hydroxide, the resulting alpha-O-protected acid may then be treated with TBAF to generate the compound of formula (I). Variation of Method H may also be apparent to those skilled in the art, for example by using an alternate intermediate G1 such as:

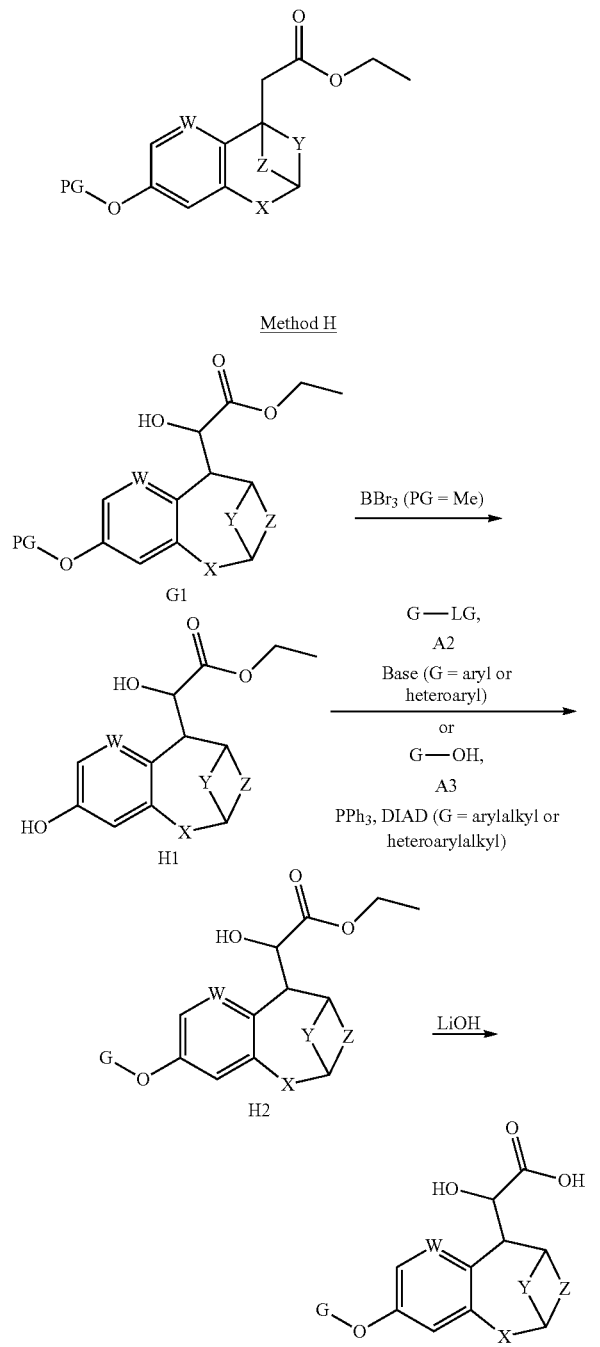

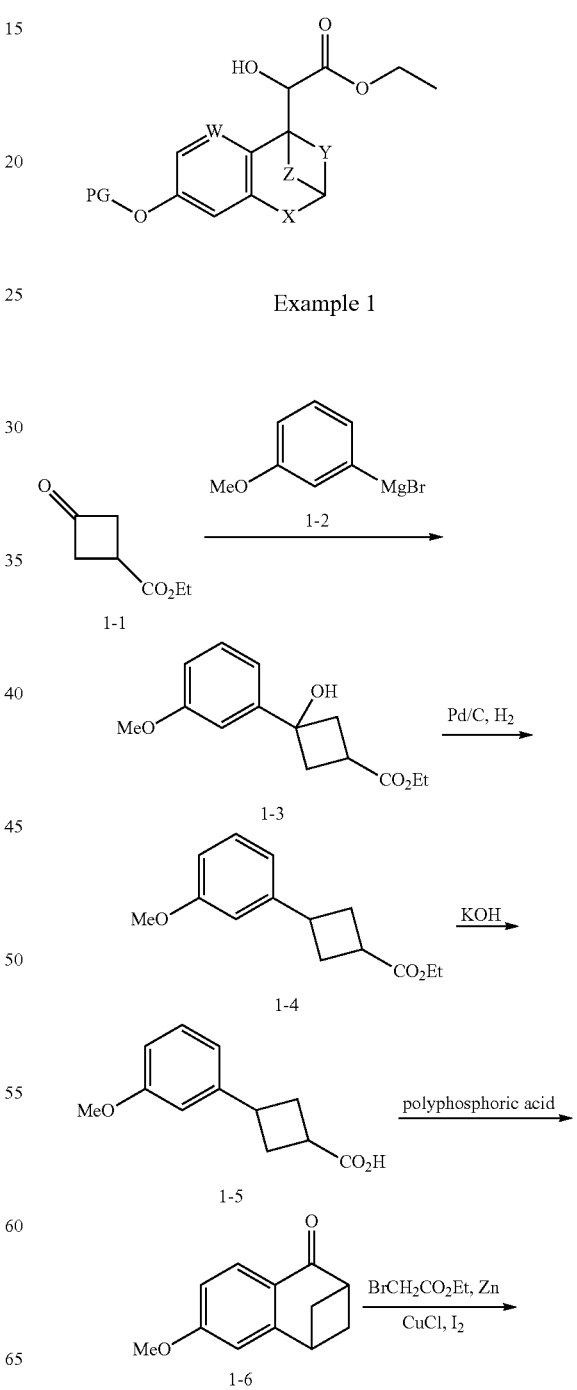

Example 1

Method H is a modification of method G to install alpha hydroxyl acids in lieu of the 2,4-thiodiazolidine dione. The protecting group in G1 is removed, for example with boron tribromide for PG=methyl, and the resulting phenol H1 is reacted following any of the processes described in Method A, as well as condition alternatives known to one skilled in the art, to give H2. H2 is then hydrolyzed with lithium hydroxide

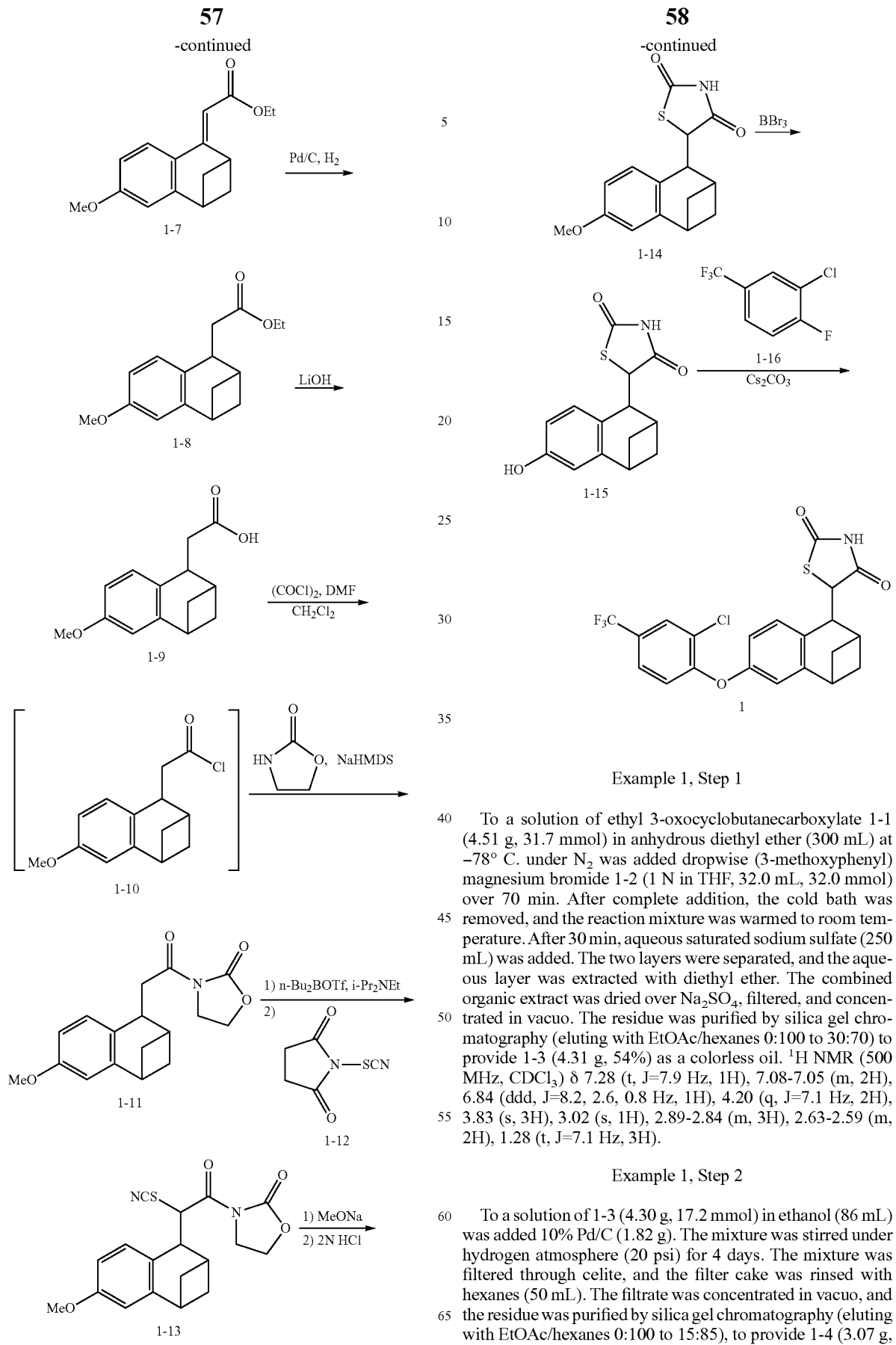

Example 1, Step 1

To a solution of ethyl 3-oxocyclobutanecarboxylate 1-1 (4.51 g, 31.7 mmol) in anhydrous diethyl ether (300 mL) at −78° C. under $N_2$ was added dropwise (3-methoxyphenyl)magnesium bromide 1-2 (1 N in THF, 32.0 mL, 32.0 mmol) over 70 min. After complete addition, the cold bath was removed, and the reaction mixture was warmed to room temperature. After 30 min, aqueous saturated sodium sulfate (250 mL) was added. The two layers were separated, and the aqueous layer was extracted with diethyl ether. The combined organic extract was dried over $Na_2SO_4$, filtered, and concentrated in vacuo. The residue was purified by silica gel chromatography (eluting with EtOAc/hexanes 0:100 to 30:70) to provide 1-3 (4.31 g, 54%) as a colorless oil. $^1$H NMR (500 MHz, $CDCl_3$) δ 7.28 (t, J=7.9 Hz, 1H), 7.08-7.05 (m, 2H), 6.84 (ddd, J=8.2, 2.6, 0.8 Hz, 1H), 4.20 (q, J=7.1 Hz, 2H), 3.83 (s, 3H), 3.02 (s, 1H), 2.89-2.84 (m, 3H), 2.63-2.59 (m, 2H), 1.28 (t, J=7.1 Hz, 3H).

Example 1, Step 2

To a solution of 1-3 (4.30 g, 17.2 mmol) in ethanol (86 mL) was added 10% Pd/C (1.82 g). The mixture was stirred under hydrogen atmosphere (20 psi) for 4 days. The mixture was filtered through celite, and the filter cake was rinsed with hexanes (50 mL). The filtrate was concentrated in vacuo, and the residue was purified by silica gel chromatography (eluting with EtOAc/hexanes 0:100 to 15:85), to provide 1-4 (3.07 g, 76%) as a colorless liquid. $^1$H NMR (500 MHz, $CDCl_3$) δ

7.22 (t, J=7.8 Hz, 1H), 6.83 (dd, J=7.6, 0.8 Hz, 1H), 6.77 (t, J=2.1 Hz, 1H), 6.75 (dd, J=8.1, 2.5 Hz, 1H), 4.15 (q, J=7.1 Hz, 2H), 3.80 (s, 3H), 3.45-3.40 (m, 1H), 3.12-3.04 (m, 1H), 2.62-2.56 (m, 2H), 2.44-2.36 (m, 2H), 1.26 (t, J=7.1 Hz, 3H).

Example 1, Step 3

To a solution of 1-4 (3.04 g, 13.0 mmol) in 70% ethanol (65 mL) was added KOH (85%, 7.28 g, 110 mmol). The solution was heated at 95° C. for 3 h, concentrated to ≈20 mL, and acidified to pH 1-2 with 1 N hydrochloric acid. The mixture was extracted with chloroform. The organic layer was dried over Na$_2$SO$_4$, filtered, and concentrated in vacuo. The residue was purified by silica gel chromatography (eluting with EtOAc/hexanes 0:100 to 40:60), to provide 1-5 (2.47 g, 92%) as a colorless oil. $^1$H NMR (500 MHz, CDCl$_3$) δ 7.23 (t, J=7.8 Hz, 1H), 6.84 (d, J=7.5 Hz, 1H), 6.78 (s, 1H), 6.75 (dd, J=8.1, 2.4 Hz, 1H), 3.80 (s, 3H), 3.49-3.43 (m, 1H), 3.18-3.11 (m, 1H), 2.66-2.61 (m, 2H), 2.48-2.41 (m, 2H).

Example 1, Step 4

A mixture of 1-5 (2.47 g, 12.0 mmol) and polyphosphoric acid (4.80 g, 48.0 mmol) under N$_2$ was heated at 90° C. for 1.5 h. Water (50 mL) was added, and the mixture stirred with a spatula until all the deep red material changed to a slightly yellow mixture. The aqueous mixture was extracted with diethyl ether. The organic extract was dried over Na$_2$SO$_4$, filtered, and concentrated in vacuo. The residue was purified by silica gel chromatography (eluting with EtOAc/hexanes 0:100 to 10:90), to provide 1-6 (1.27 g, 56%) as a yellow oil. $^1$H NMR (500 MHz, CDCl$_3$) δ 7.94 (d, J=8.5 Hz, 1H), 6.83 (dd, J=8.5, 2.4 Hz, 1H), 6.72 (d, J=2.4 Hz, 1H), 3.86 (s, 3H), 3.27 (q, J=4.6 Hz, 1H), 3.15 (q, J=5.8 Hz, 1H), 2.93-2.88 (m, 2H), 2.34-2.31 (m, 2H).

Example 1, Step 5

A mixture of 1-6 (1.27 g, 6.75 mmol), zinc dust (1.58 g, 24.3 mmol), copper(I) chloride (66 mg, 0.68 mmol) and I$_2$ (1 crystal) in THF (29 mL) was heated at 65° C. under N$_2$ for 15 min. Ethyl bromoacetate (3.38 g, 20.2 mmol) was added dropwise over 5 min. The mixture was heated at 65° C. overnight. The oil bath temperature was increased to 70° C., and additional zinc dust (1.58 g, 24.3 mmol) and copper(I) chloride (66 mg, 0.68 mmol) were added. After 10 min, additional ethyl bromoacetate (3.38 g, 20.2 mmol) was added dropwise. The reaction was heated at reflux for 4 h, cooled to room temperature, and filtered through celite. The filter cake was washed with DCM (30 mL). The filtrate was concentrated in vacuo, and the residue was dissolved in EtOAc (50 mL). The pH was adjusted to ≈1 with hydrochloric acid (1 N), and the two layers were separated. The aqueous layer was extracted with EtOAc and the combined organic layers were dried over Na$_2$SO$_4$, filtered, and concentrated in vacuo. The residue was purified by silica gel chromatography (eluting with EtOAc/hexanes 0:100 to 5:95), to provide 1-7 (971 mg, 55%) as a pale yellow oil. $^1$H NMR (500 MHz, CDCl$_3$) δ 7.70 (d, J=8.7 Hz, 1H), 6.75 (dd, J=7.6, 2.6 Hz, 1H), 6.63 (d, J=2.6 Hz, 1H), 6.25 (s, 1H), 4.88 (q, J=6.0 Hz, 1H), 4.19 (q, J=6.8 Hz, 2H), 3.82 (s, 3H), 3.15 (q, J=5.4 Hz, 1H), 2.69-2.65 (m, 2H), 1.86-1.84 (m, 2H), 1.31 (t, J=7.0 Hz, 3H).

Example 1, Step 6

A mixture of 1-7 (500 mg, 1.94 mmol) and 10% Pd/C (205 mg, 0.194 mmol) in ethanol (19 mL) was stirred under hydrogen atmosphere (30 psi) for 4 days. The mixture was filtered through celite. The filter cake was washed with DCM (30 mL). The filtrate was concentrated to give 1-8 (506 mg, 100%) as a yellow liquid, which was used in the next step without further purification. $^1$H NMR (500 MHz, CDCl$_3$) δ 7.13 (d, J=8.4 Hz, 1H), 6.71 (dd, J=8.3, 2.7 Hz, 1H), 6.56 (d, J=2.6 Hz, 1H), 4.19 (q, J=7.1 Hz, 2H), 3.77 (s, 3H), 3.57-3.55 (m, 1H), 3.04 (q, J=4.6 Hz, 1H), 2.80 (dd, J=15.4, 4.4 Hz, 1H), 2.64-2.63 (m, 1H), 2.49-2.43 (m, 2H), 2.28-2.25 (m, 1H), 1.51-1.49 (m, 2H), 1.28 (t, J=7.1 Hz, 3H).

Example 1, Step 7

To a solution of 1-8 (300 mg, 1.15 mmol) in ethanol (11 mL) was added lithium hydroxide monohydrate (386 mg, 9.2 mmol) and water (1 mL). The mixture was heated at 50° C. for 3 h. The solvent was evaporated in vacuo, and the residue was diluted with chloroform (20 mL) and acidified with hydrochloric acid (1 N) to pH≈1 at 0° C. The two layers were separated, and the aqueous layer was extracted with chloroform. The combined organic extract was dried over Na$_2$SO$_4$, filtered, and concentrated. The residue was purified by silica gel chromatography (eluting with EtOAc/hexanes 0:100 to 40:60), to provide 1-9 (264 mg, 98%) as a white solid. $^1$H NMR (500 MHz, CDCl$_3$) δ 7.16 (d, J=8.3 Hz, 1H), 6.73 (dd, J=8.3, 2.6 Hz, 1H), 6.57 (d, J=2.6 Hz, 1H), 3.78 (s, 3H), 3.59-3.57 (m, 1H), 3.05 (q, J=5.4 Hz, 1H), 2.88 (dd, J=15.8, 4.2 Hz, 1H), 2.72-2.70 (m, 1H), 2.54 (dd, J=15.9, 10.2 Hz, 1H), 2.49-2.45 (m, 1H), 2.31-2.27 (m, 1H), 1.54-1.48 (m, 2H).

Example 1, Step 8

Oxalyl chloride (30 µL, 0.36 mmol) was added dropwise to a solution of 1-9 (70 mg, 0.30 mmol) and DMF (1 drop) in DCM (0.6 mL) at 0° C. under N$_2$. The mixture was stirred at room temperature for 1 h and concentrated to ≈0.2 mL to give crude 1-10. In a separate flask containing 2-oxazolidinone (47 mg, 0.54 mmol) was added anhydrous THF (1 mL). The flask was cooled to −42° C. and sodium bis(trimethylsilyl)amide (1 M in THF, 0.60 mL, 0.60 mmol) was added dropwise. The cold bath was removed, and the yellow mixture was stirred for 10 min. The mixture was then cooled to −42° C. A solution of crude 1-10 in THF (0.7 mL) was added dropwise. The reaction was stirred at −42° C. for 30 min, warmed to room temperature, and stirred for 3 h. The reaction was diluted with saturated aqueous ammonium chloride (15 mL) at 0° C. and extracted with EtOAc. The organic extract was dried over Na$_2$SO$_4$, filtered, and concentrated in vacuo. The residue was purified by silica gel chromatography (eluting with EtOAc/hexanes 0:100 to 30:70) to provide 1-11 (82 mg, 90%) as a white solid. $^1$H NMR (500 MHz, CDCl$_3$) δ 7.25 (d, J=8.8 Hz, 1H), 6.72 (dd, J=8.3, 2.7 Hz, 1H), 6.56 (d, J=2.6 Hz, 1H), 4.43 (t, J=7.8 Hz, 2H), 4.06 (t, J=7.9 Hz, 2H), 3.77 (s, 3H), 3.66 (td, J=10.0, 3.0 Hz, 1H), 3.48 (dd, J=16.2, 3.5 Hz, 1H), 3.14-3.01 (m, 2H), 2.67-2.60 (m, 1H), 2.47-2.41 (m, 1H), 2.30-2.24 (m, 1H), 1.59-1.47 (m, 2H).

Example 1, Step 9

N-thiocyanatosuccinimide reagent 1-12 was prepared according to Toste, F. et al *Synth. Commun.* 1995, 25, 1277. Di-n-butylboron triflate (1 M in DCM, 0.26 mL, 0.26 mmol) was added dropwise to a solution of 1-11 (72 mg, 0.24 mmol) in anhydrous DCM (1.8 mL) under N$_2$ at 0° C. Diisopropylethylamine (48 µL, 0.28 mmol) was added dropwise. The slightly yellow mixture was stirred at 0° C. for 1 h, and then cooled to −78° C. A solution of 1-12 (90 mg, ~0.50 mmol) in DCM (1 mL) was added dropwise. The mixture was stirred at −78° C. for 2 h, warmed to room temperature, and then quenched with pH 7 buffer [3 mL, prepared by dissolving NaH$_2$PO$_4$ (1.20 g) and Na$_2$HPO$_4$ dodecahydrate (2.23 g) in water (50 mL)] and aqueous H$_2$O$_2$ (35%, 0.2 mL). The mixture was stirred for 30 min and extracted with EtOAc. The organic extract was dried over Na$_2$SO$_4$, filtered, and concentrated in vacuo. The residue was purified by silica gel chromatography (eluting with EtOAc/hexanes 0:100 to 50:50) to provide a mixture (73 mg) of 1-11 and 1-13, which was further purified by prep-HPLC (XBridge ODB C18 5 μm, 30×150 mm, 43 mL/min, acetonitrile/water 10:90 to 90:10) to provide 1-11 (34 mg, 47%) and 1-13 (27 mg, 31%, dr 7:3) as a white solid. 1-13: $^1$H NMR (500 MHz, CDCl$_3$) δ 7.54 (d, J=8.3 Hz, 0.3H), 7.04 (d, J=8.4 Hz, 0.7H), 6.75 (dd, J=8.5, 2.8 Hz, 0.3H), 6.63 (dd, J=8.4, 2.7 Hz, 0.7H), 6.60 (s, 0.7H), 6.59 (s, 0.3H), 5.48 (d, J=7.8 Hz, 0.3H), 5.42 (d, J=9.4 Hz, 0.7H), 4.52-4.40 (m, 2H), 4.25-4.08 (m, 2H), 3.93 (dd, J=9.3, 3.0 Hz, 0.7H), 3.81-3.79 (m, 0.3H), 3.79 (s, 0.9H), 3.77 (s, 2.1H), 3.15-3.12 (m, 0.7H), 3.08-3.04 (m, 1H), 2.80-2.77 (m, 0.3H), 2.58 (td, J=9.1, 5.8 Hz, 0.7H), 2.50 (td, J=9.1, 6.0 Hz, 0.3H), 2.37 (td, J=9.7, 5.8 Hz, 0.7H), 2.29 (td, J=9.7, 5.8 Hz, 0.3H), 1.72 (q, J=8.3 Hz, 1H), 1.50-1.46 (m, 1H).

Example 1, Step 10

Sodium methoxide (25% in methanol, 41 μL, 0.18 mmol) was added dropwise to a solution of 1-13 (25 mg, 0.070 mmol) in methanol/THF (3.5 mL, 4:1, v/v) at 0° C. under N$_2$. The cold bath was removed, and the mixture was stirred at room temperature for 1 h. Hydrochloric acid (2 N) was added until the solution reached pH≈2. The mixture was stirred for 3 h, diluted with water (8 mL), and extracted with EtOAc (3×10 mL). The organic extract was dried over Na$_2$SO$_4$, filtered, and concentrated in vacuo. The residue was purified by silica gel chromatography (eluting with EtOAc/hexanes 0:100 to 40:60) to provide 1-14 (10 mg, 50%, dr 1:1) as a white semisolid. $^1$H NMR (500 MHz, CDCl$_3$) δ 7.96 (br s, 0.5H), 7.92 (br s, 0.5H), 7.18 (d, J=8.4 Hz, 0.5H), 6.97 (d, J=8.4 Hz, 0.5H), 6.75 (dd, J=8.3, 2.7 Hz, 0.5H), 6.69 (dd, J=8.4, 2.7 Hz, 0.5H), 6.61-6.60 (m, 1H), 5.15 (d, J=4.3 Hz, 0.5H), 4.57 (d, J=2.3 Hz, 0.5H), 4.19 (br s, 0.5H), 4.06 (br s, 0.5H), 3.79 (s, 1.5H), 3.78 (s, 1.5H), 3.05-3.01 (m, 1H), 2.82-2.80 (m, 0.5H), 2.73-2.69 (m, 0.5H), 2.55-2.51 (m, 1H), 2.37-2.33 (m, 0.5H), 2.29-2.25 (m, 0.5H), 2.03 (t, J=8.8 Hz, 0.5H), 1.61-1.58 (m, 1.5H).

Example 1, Step 11

Boron tribromide (1 M in hexanes, 90 μL, 90 μmol) was added to a solution of 1-14 (8.8 mg, 30 μmol) in DCM (0.3 mL) at −78° C. under N$_2$. The cold bath was removed, and the orange mixture was stirred at room temperature for 1 h. Methanol (0.5 mL) was added, and the mixture stirred for 5 min. The mixture was concentrated in vacuo, and the residue was dried under high vacuum for 1 h to give 1-15 (10 mg, >99%) as a slightly brown solid, which was used in the next step without further purification.

Example 1, Step 12

2-Chloro-1-fluoro-4-(trifluoromethyl)benzene 1-16 (7.0 mg, 36 μmol), 1-15 (10 mg, ≈30 μmol), cesium carbonate (29 mg, 90 μmol), and N,N-dimethylacetamide (0.3 mL) were added to a pressure tube and flushed with N$_2$. The tube was quickly sealed, and placed in a pre-heated oil bath (120° C.).

The mixture was stirred for 30 min, cooled to room temperature, and acidified with hydrochloric acid (1 N) to pH≈1. The mixture was extracted with EtOAc. The organic extract was dried over Na$_2$SO$_4$, filtered, and concentrated in vacuo. The residue was purified by silica gel chromatography (eluting with EtOAc/hexanes 0:100 to 30:70) to provide Example 1 (9 mg, 67%, dr 1:1) as a pale yellow solid. $^1$H NMR (500 MHz, CDCl$_3$) δ 7.91 (s, 1H), 7.73 (dd, J=5.6, 1.8 Hz, 1H), 7.46-7.45 (m, 1H), 7.29-7.28 (m, 0.5H), 7.06-7.03 (m, 0.5H), 7.01 (d, J=9.2 Hz, 1H), 6.88 (dd, J=8.2, 2.5 Hz, 0.5H), 6.82 (dd, J=8.3, 2.5 Hz, 0.5H), 6.73-6.72 (m, 1H), 5.15 (d, J=4.2 Hz, 0.5H), 4.60 (d, J=2.2 Hz, 0.5H), 4.24 (s, 0.5H), 4.11 (s, 0.5H), 3.06-3.03 (m, 1H), 2.86-2.84 (m, 0.5H), 2.75-2.74 (m, 0.5H), 2.58-2.53 (m, 1H), 2.41-2.36 (m, 0.5H), 2.31-2.29 (m, 0.5H), 2.05-2.02 (m, 0.5H), 1.64-1.61 (m, 1.5H). MS (ESI) m/z: 452.2 [M-H]$^-$. MP: 77-80° C. HPLC>99%, t$_R$=26.3 & 26.5 min.

The compounds in Table 1 were prepared following procedures similar to those of Example 1, including using intermediates described in UK Pat. Appl. (1994), GB 2276379 and separing the enantiomers of intermediate 1-8 via chiral preparative HPLC.

TABLE 1

| Example No. | COMPOUND | Mass Spec (M − H)$^-$; retention time (min) |
|---|---|---|
| 1-A | | 510.3; 27.1 & 27.3 |
| 1-B | | 452.2; 26.2 & 26.4 |
| 1-C | | 510.3; 26.9 & 27.1 |

TABLE 1-continued

| Example No. | COMPOUND | Mass Spec (M − H)⁻; retention time (min) |
|---|---|---|
| 1-D | | 409.4; 22.6 |
| 1-E | | 470.6; 22.8 |
| 1-F | | 427.1; 20.4 & 20.6 |

Example 2

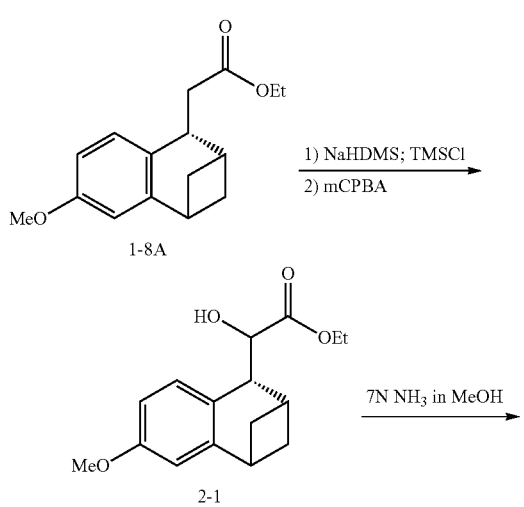

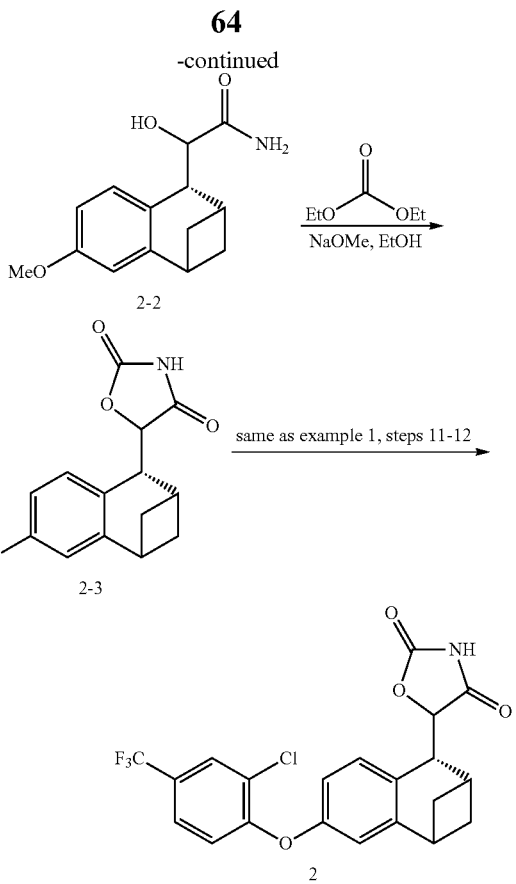

Example 2, Step 1

Intermediate 1-8 from Example 1 was separated by chiral preparative HPLC to give enantiomer 1-8A. This enantiomer was treated with sodium hexamethyldisylazide in THF at −78° C. followed by addition of chloro trimethylsilane and warming to room temperature to give an intermediate enol silane. This enol silane was treated with meta-chloroperoxybenzoic acid from −7° C. to room temperature followed by treatment with TBAF to provide compound 2-1 after workup and purification by silica gel chromatography.

Example 2, Step 2

Compound 2-1 was reacted with 7N ammonia in methanol at room temperature for 2 days to provide compound 2-2 after purification by silica gel chromatography.

Example 2, Step 3

Compound 2-1 was reacted with ethyl carbonate and sodium methoxide in anhydrous ethanol at 95° C. to provide compound 2-3 after workup and purification by silica gel chromatography.

Example 2, Step 4

Compound 2-3 was subjected to conditions described in Example 1, steps 11 and 12 to provide Example 2 after workup and purification by silica gel chromatography. ¹H NMR (500 MHz, CDCl₃) δ 7.74 (m, 1H), 7.60 (s, 1H), 7.46-7.45 (m, 1H), 7.36-7.35 (m, 0.5H), 7.28-7.26 (m, 1H), 7.03-7.00 (m, 1H), 6.91-6.89 (m, 0.5H), 6.83-6.82 (m, 0.5H), 6.74-6.73 (m, 1H), 5.47 (br s, 0.5H), 5.04 (br s, 0.5H), 3.79 (s, 0.5H), 3.77 (s, 0.5H), 3.08-3.05 (m, 1H), 3.02-2.99 (m, 0.5H), 2.74-2.72 (m, 0.5H), 2.60-2.58 (m, 1H), 2.39-2.35 (m, 1H), 1.88-1.84 (m, 1H), 1.60-1.55 (m, 1H). MS (ESI) m/z: 436.4 [M-H]$^-$. HPLC>99%, $t_R$=24.8.

Example 3

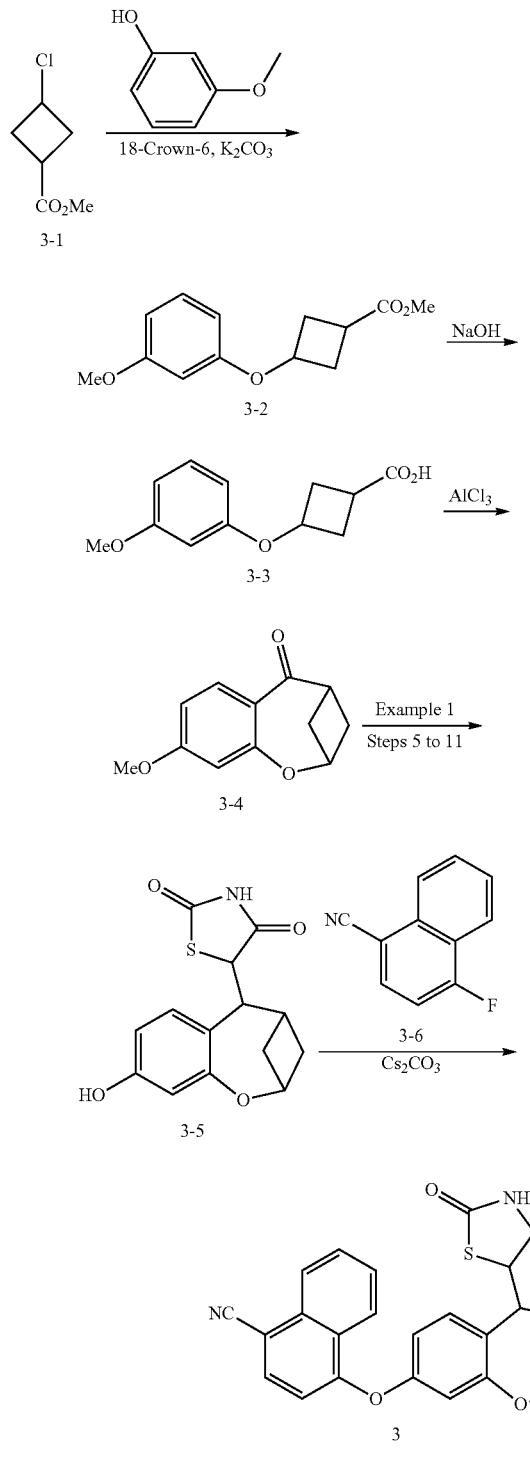

Example 3, Step 1

Methyl 3-chlorocyclobutane carboxylate 3-1 is coupled with 3-methoxyphenol following conditions similar to the ones described in US 2004/026482 to provide compound 3-2 as a cis and trans mixture, after workup and purification

Example 3, Step 2

Compound 3-2 is hydrolyzed with sodium hydroxide in aqueous isopropanol followed by neutralization with aqueous HCl and extraction to give compound 3-3 as a cis and trans mixture, after purification.

Example 3, Step 3

Treatment of 3-3 with aluminum chloride in DCE, or an alternative method such as trifluoroacetic anhydride followed by acidic aqueous treatment, yields compound 3-4 after workup and purification in addition to unreacted trans reagent.

Example 3, Step 4

Compound 2-4 is converted into compound 2-5 following conditions similar to the ones described in Example 1, Steps 5 to 11.

Example 3, Step 5

Reaction of compound 3-5 with 4-fluoronaphthonitrile 3-6 and cesium carbonate in DMF affords Example 3 after workup and purification.

Example 4

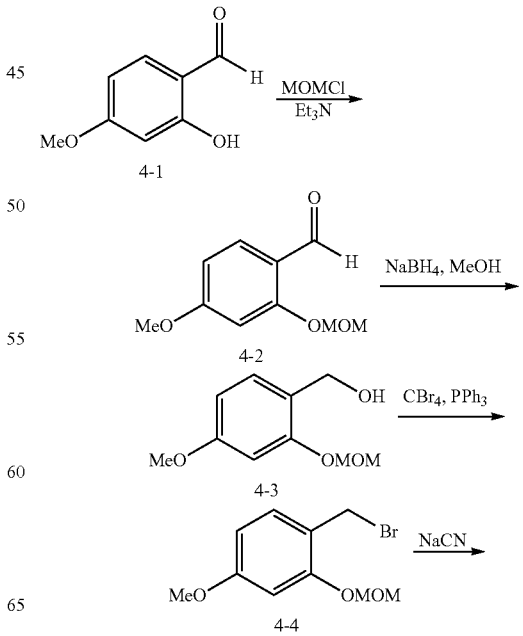

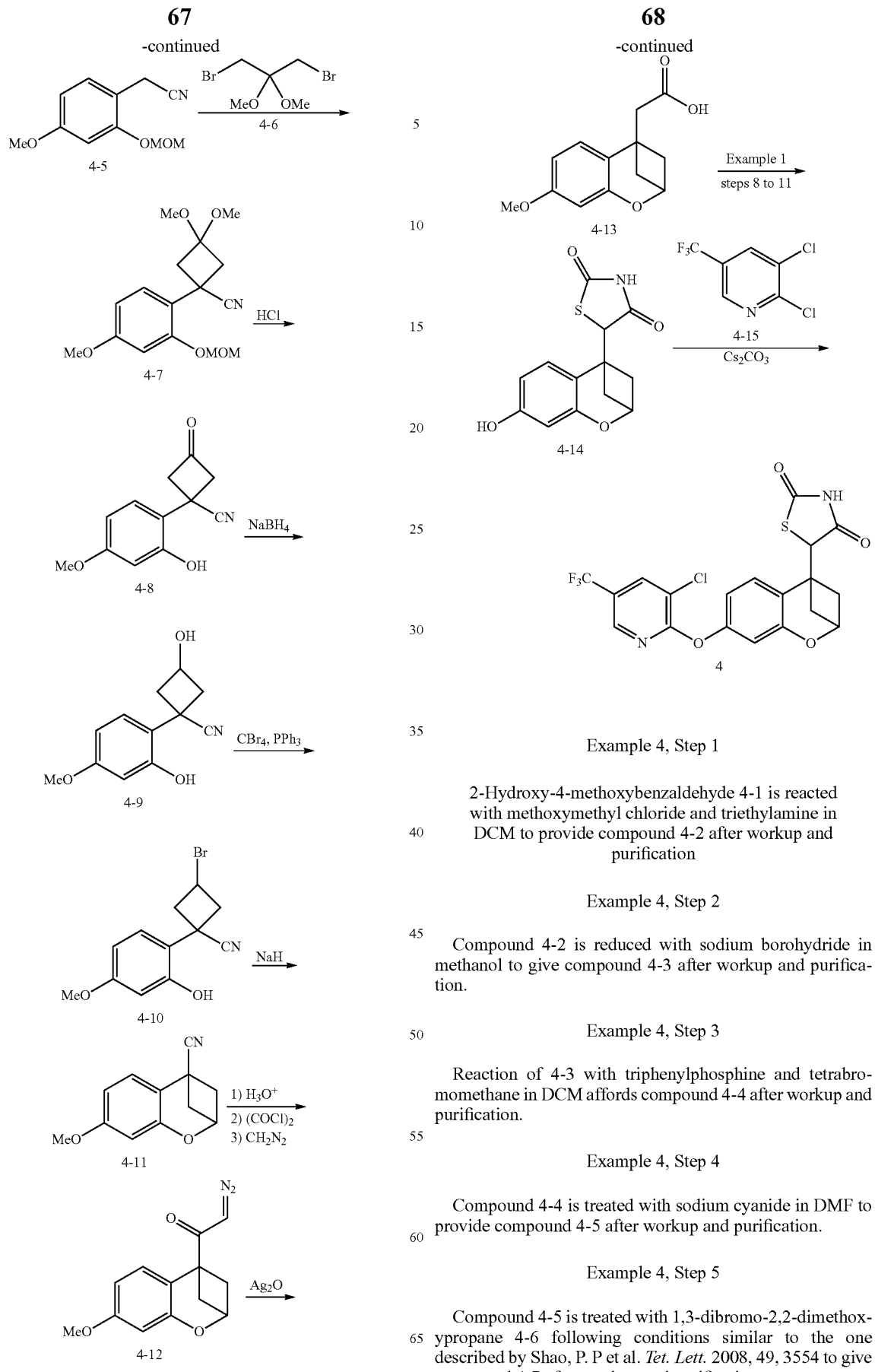

Example 4, Step 1

2-Hydroxy-4-methoxybenzaldehyde 4-1 is reacted with methoxymethyl chloride and triethylamine in DCM to provide compound 4-2 after workup and purification

Example 4, Step 2

Compound 4-2 is reduced with sodium borohydride in methanol to give compound 4-3 after workup and purification.

Example 4, Step 3

Reaction of 4-3 with triphenylphosphine and tetrabromomethane in DCM affords compound 4-4 after workup and purification.

Example 4, Step 4

Compound 4-4 is treated with sodium cyanide in DMF to provide compound 4-5 after workup and purification.

Example 4, Step 5

Compound 4-5 is treated with 1,3-dibromo-2,2-dimethoxypropane 4-6 following conditions similar to the one described by Shao, P. P et al. *Tet. Lett.* 2008, 49, 3554 to give compound 4-7 after workup and purification.

Example 4, Step 6

Hydrolysis of compound 4-7 gives compound 4-8 after purification.

Example 4, Step 7

Compound 4-8 is reduced with sodium borohydride in methanol to provide compound 4-9 after workup and purification.

Example 4, Step 8

Reaction of 4-9 with triphenylphosphine and tetrabromomethane in DCM affords compound 4-10 after workup and purification.

Example 4, Step 9

Treatment of 4-10 with a base such as NaH in a solvent such as DMF affords compound 4-11 after workup and purification.

Example 4, Step 10

Compound 4-11 is hydrolysed under acidic conditions to an acid which is then treated with oxalyl chloride in DCM with a drop of DMF to afford an acyl chloride intermediate. This acyl chloride intermediate is then treated with diazomethane in DCM, optionally in the presence of triethylamine, to give compound intermediate 4-12.

Example 4, Step 11

Arndt-Eistert rearrangement of 4-12 with silver oxide in water results in compound 4-13 after workup and purification.

Example 4, Step 12

Compound 4-13 is converted into compound 4-14 following conditions similar to the ones described in Example 1, Steps 8 to 11.

Example 4, Step 12

Reaction of compound 4-14 with 2,3-dichloro-5-(trifluoromethyl)pyridine and cesium carbonate in DMF affords Example 4 after workup and purification.

GPR40 Primary FLIPR Assay:

The cDNA encoding the human GPR40 receptor was subcloned into the pcDNA3.1 expression vector and stably transfected into HEK 293 cells using Lipofectamine 2000. Cells stably expressing the hGPR40 receptor were harvested and plated into poly-D-lysine coated 384 well plates at a concentration 8,000 cells/well and incubated for approximately 24 hours in a 37° C. incubator with 5% $CO_2$. On the day of the experiment, FLIPR Buffer A was prepared by combining 20 mM Hepes, 0.04% CHAPS and 2.5 mM probenecid with Hanks Buffer. Molecular probes Calcium 4 Dye was then diluted 1:20 into FLIPR buffer A using manufacturers instructions to make the cell dye-loading buffer. Medium was removed from the cells, after which 35 µl of dye-loading buffer was added. The plates were incubated at 37° C. in a 5% $CO_2$ incubator for 1 hour, after which then were left at room temperature for another hour. Plates were then placed in the FLIPR 384 and 5 µl of an 8× concentration of compound was added by the FLIPR robotics.

Maximum fluorescence response at each concentration of compound was determined by the FLIPR384 software. Maximum Fluorescence for each concentration was then compared with the response seen in the absence of compound (% control), and the $EC_{50}$ for an increase in baseline fluorescence in the presence of compound was calculated using Microsoft Excel Fit software. The maximum fluorescent response of the compound was also compared to that seen in the presence of a 30 uM concentration of a standard compound and a percent maximum response was calculated. Data were reported for both $EC_{50}$ and % Maximum response.

The compounds had an $EC_{50}$ higher than 20 nM and less than 1 µM. The compound has a maximum response higher than 50%.

While the present invention has been described in conjunction with the specific embodiments set forth above, many alternatives, modifications and variations thereof will be apparent to those of ordinary skill in the art. All such alternatives, modifications, and variations are intended to fall within the spirit and scope of the present invention.

What we claim is:

1. A compound which is represented by the structural formula

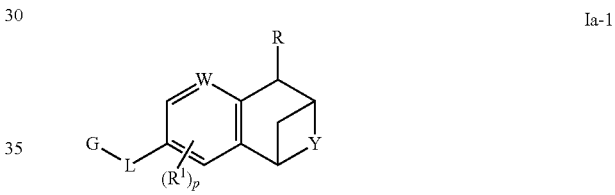

Ia-1 or a pharmaceutically acceptable salt thereof wherein
G is aryl, aryl alkyl, heteroaryl, or heteroarylalkyl, which is optionally substituted by at least one $R^2$;
L is —O—, —C(O)—, —S(O)$_q$—, or —N($R^3$)—;
W is —C— or —N—;
Y is a bond, -[C($R^a$)($R^b$)]$_n$—O—[C($R^a$)($R^b$)]$_n$, -[C($R^a$)($R^b$)]$_n$—C(O)-[C($R^a$)($R^b$)]$_n$, -[C($R^a$)($R^b$)]$_n$—S(O)$_q$-[C($R^a$)($R^b$)]$_n$, -[C($R^a$)($R^b$)]$_m$- or —N($R^8$)—;
R is a group selected from the group consisting of

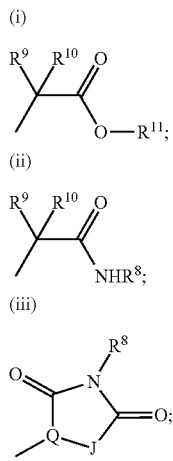

-continued (iv)

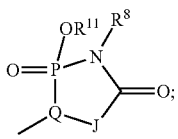

and
(v) tetrazolyl,
wherein
Q is —CH— or —N—, and
J is —S—, —CH$_2$—, —O— or —N(R$^8$)—;

R$^a$ is independently selected from the group consisting of H, —OH, halo, alkoxy, alkyl, cycloalkyl, and cycloalkylalkyl;

R$^b$ is independently selected from the group consisting of H, —OH, halo, alkoxy, alkyl, cycloalkyl, and cycloalkylalkyl;

R$^1$ is independently selected from the group consisting of H, halogen, —SF$_5$, —S(O)$_q$-alkyl, —CN, —NO$_2$, —N(R$^6$)(R$^7$), —OH, alkyl, alkoxy, cycloalkyl, cycloalkyloxy, cycloalkylalkyl, and cycloalkylalkoxy wherein said alkyl, alkoxy, cycloalkl, cycloalkyloxy, cycloalkylalkyl, and cycloalkylalkoxy are optionally substituted with one or more groups selected from the group consisting of —OH, halo, —S(O)$_q$-alkyl, alkyl, haloalkyl, alkoxy, haloalkoxy, and cycloalkyl;

R$^2$ is independently selected from the group consisting of halogen, —SF$_5$, —CN, —NO$_2$, —N(R$^6$)(R$^7$), —OH, alkyl, alkoxy, cycloalkyl, cycloalkyloxy, cycloalkylalkyl, cycloalkylalkoxy, aryl, arylalkyl, heteroaryl, heteroarylalkyl and —S(O)$_q$-alkyl, wherein said alkyl, alkoxy, cycloalkyl, cycloalkyloxy, cycloalkylalkyl, cycloalkylalkoxy, aryl, arylalkyl, heteroaryl, and heteroarylalkyl are optionally substituted with one or more groups selected from the group consisting of —OH, halo, alkyl, —S(O)$_q$-alkyl, haloalkyl, alkoxy, haloalkoxy, and cycloalkyl;

R$^3$ is independently selected from the group consisting of H, alkyl, haloalkyl;

R$^4$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

R$^5$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

R$^6$ is independently selected from the group consisting of H, alkyl, cycloalkyl, cycloalkylalkyl, aryl, arylalkyl, heterocycloalkyl, heterocycloalkylalkyl, heteroaryl and heteroarylalkyl;

R$^7$ is independently selected from the group consisting of H, alkyl, cycloalkyl, cycloalkylalkyl, aryl, arylalkyl, heterocycloalkyl, heterocycloalkylalkyl, heteroaryl, and heteroarylalkyl;

or R$^6$ and R$^7$ together form a 4- to 7-membered heterocycloalkyl or a 5- or 5-membered heteroaryl ring optionally having, in addition to the N atom, 1 or 2 heteroatoms selected from the group consisting of O, N(R$^8$), N or S, wherein said rings are optionally substituted by one or more R$^{12}$ moieties;

R$^8$ is independently selected from the group consisting of H, alkyl, cycloalkyl, cycloalkylalkyl, aryl, arylalkyl, heterocycloalkyl, heterocycloalkylalkyl, heteroaryl, heteroarylalkyl, —C(O)—R$^5$, —C(O)O—R$^5$, —C(O)N(R$^6$)(R$^7$), —C(O)-alkylene-OR$^4$, —C(O)— alkylene-N(R$^6$)(R$^7$), —C(O)-alkylene-S(O)$_q$—R$^5$, —S(O)$_q$—R$^5$, —S(O)$_q$-alkylene-OR$^4$, —S(O)$_q$-alkylene-N(R$^6$)(R$^7$), -alkylene-OR$^4$, -alkylene-S(O)$_q$—R$^5$, -alkylene-N(R$^6$)(R$^7$), and —S(O)$_2$N(R$^6$)(R$^7$) wherein said alkyl, cycloalkyl, cycloalkylalkyl, aryl, arylalkyl, heterocycloalkyl, heterocycloalkylalkyl, heteroaryl, heteroarylalkyl and alkylene are optionally substituted with one or more groups selected from the group consisting of —OH, halo, alkyl, haloalkyl, alkoxy, haloalkoxy and cycloalkyl;

R$^9$ is independently selected from the group consisting of H, alkyl, haloalkyl;

R$^{10}$ is independently selected from the group consisting of H, —OH, alkyl, alkyl, cycloalkyl or alkoxy wherein said alkyl, alkyl, cycloalkyl or alkoxy groups are optionally substituted with at least one substituent selected from the group consisting of halo and —OR$^5$;

R$^{11}$ is independently selected from the group consisting of H, alkyl, and haloalkyl;

wherein each of the alkyl, cycloalkyl, cycloalkylalkyl, aryl, arylalkyl, heterocycloalkyl, heterocycloalkylalkyl, heteroaryl, and heteroarylalkyl groups in R$^4$, R$^5$, R$^6$, and R$^7$ are independently unsubstituted or substituted by one or more R$^{12}$ groups, where R$^{12}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —C(O)N(R$^6$)(R$^7$), and —S(O)$_2$N(R$^6$)(R$^7$), —NO$_2$, —SF$_5$, —CN, —N(R$^6$)(R$^7$) and halo and wherein each alkyl, cycloalkyl, cycloalkylalkyl, aryl, arylalkyl, heterocycloalkyl, heterocycloalkylalkyl, heteroaryl, and heteroarylalkyl group in R$^{12}$ is independently unsubstituted or substituted by one or more R$^{13}$ groups, where R$^{13}$ is independently selected from the group consisting of alkyl, cycloalkyl, cycloalkylalkyl, aryl, arylalkyl, heterocycloalkyl, heterocycloalkylalkyl, heteroaryl, heteroarylalkyl, —OR$^4$, —C(O)—R$^5$, —C(O)O—R$^5$, —S(O)$_q$—R$^5$, —C(O)N(R$^6$)(R$^7$), and —S(O)$_2$N(R$^6$)(R$^7$), —NO$_2$, —SF$_5$, —CN, and halo;

m is independently 1, 2, or 3;

n is independently 0, 1 or 2;

q is independently 0, 1, or 2; and p is 0, 1,2,or 3.

2. The compound according to claim 1 which is a compound selected from the group consisting of

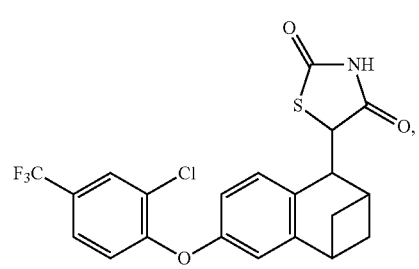

-continued

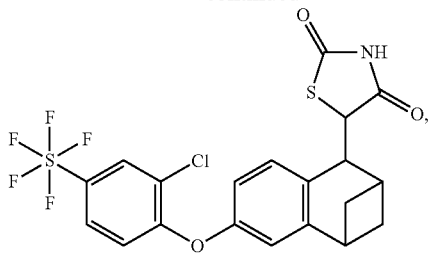

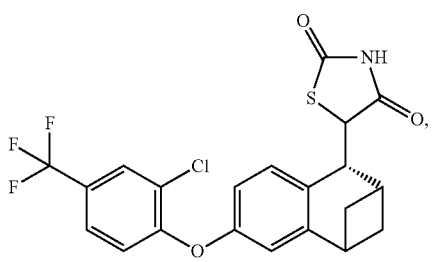

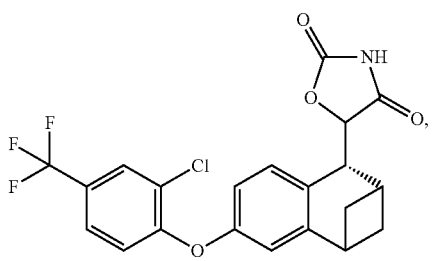

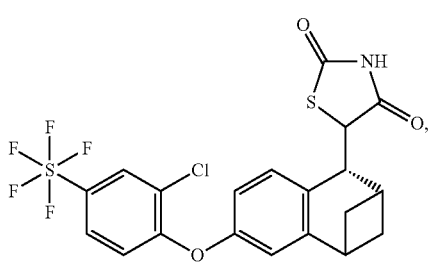

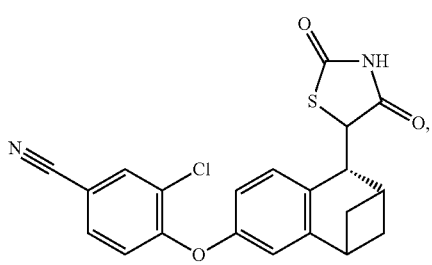

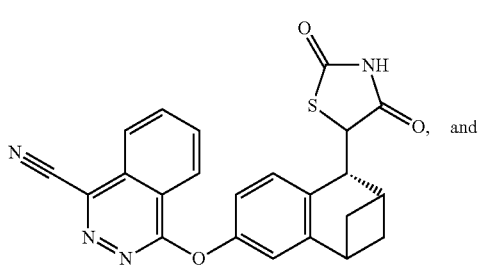 and

-continued

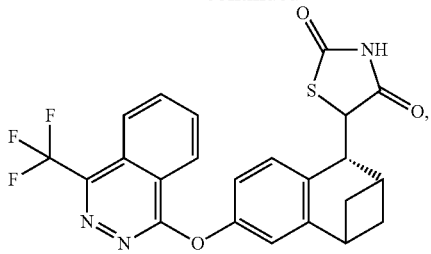 [SMILES: O=C1NC(=O)C([C@H]2c3ccc(Oc4nnc(C(F)(F)F)c5ccccc45)cc3C3CC2C3)S1]

or a pharmaceutically acceptable salt thereof.

3. The compound according to claim 1 wherein W is —CH—; or a pharmaceutically acceptable salt thereof.

4. The compound according to claim 3 wherein R is

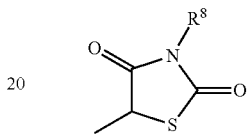

and $R^8$ is H or —($C_1$-$C_4$)alkyl; or a pharmaceutically acceptable salt thereof.

5. The compound according to claim 4, wherein Y is —$CH_2$—; or a pharmaceutically acceptable salt thereof.

6. The compound which is:

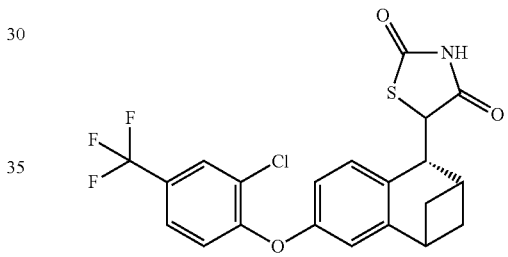

or a pharmaceutically acceptable salt thereof.

7. The compound which is:

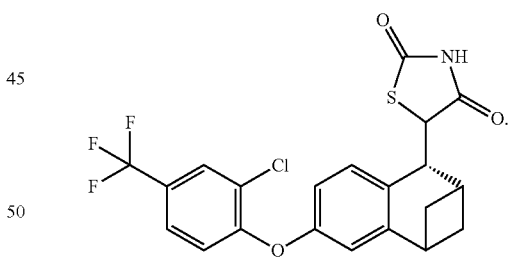

8. A pharmaceutical composition comprising a pharmaceutically effective amount of a compound according to claim 1 or a pharmaceutically acceptable salt thereof and a pharmaceutically acceptable carrier.

9. A method for controlling insulin levels in a mammal in need thereof which comprises administering an effective amount of a compound according to claim 1 or a pharmaceutically acceptable salt thereof to said mammal.

10. A method for the treatment of Type-2 diabetes mellitus in a mammal in need thereof which comprises administering an effective amount of a compound according to claim 1 or a pharmaceutically acceptable salt thereof to said mammal.

\* \* \* \* \*